US009851369B2

(12) United States Patent
Reisch et al.

(10) Patent No.: US 9,851,369 B2
(45) Date of Patent: *Dec. 26, 2017

(54) STORAGE AND SUPPLY FOR VESSEL HOLDERS

(71) Applicant: Roche Diagnostics Operations, Inc., Indianapolis, IN (US)

(72) Inventors: Dietmar Reisch, Udligenswil (CH); Gottlieb Schacher, Kriens (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/599,080

(22) Filed: May 18, 2017

(65) Prior Publication Data

US 2017/0254825 A1    Sep. 7, 2017

Related U.S. Application Data

(63) Continuation of application No. 14/567,531, filed on Dec. 11, 2014.

(30) Foreign Application Priority Data

Dec. 19, 2013  (EP) .................................... 13198403

(51) Int. Cl.
*B65G 65/00*    (2006.01)
*G01N 35/00*    (2006.01)
(Continued)

(52) U.S. Cl.
CPC ........... *G01N 35/025* (2013.01); *B65G 65/00* (2013.01); *G01N 1/28* (2013.01); *G01N 33/00* (2013.01);
(Continued)

(58) Field of Classification Search
CPC ............ G01N 1/28; G01N 2035/0462; G01N 2035/0465; G01N 2035/0467;
(Continued)

(56) References Cited

U.S. PATENT DOCUMENTS

| 3,986,028 A | 10/1976 | Byrd |
| 5,080,865 A | 1/1992 | Leiner et al. |

(Continued)

FOREIGN PATENT DOCUMENTS

EP    2485058 A1    8/2012

*Primary Examiner* — Jennifer Wecker
(74) *Attorney, Agent, or Firm* — Roche Diagnostics Operations, Inc.

(57) ABSTRACT

An automated system and method for processing vessels containing biological samples are presented. The system comprises vessel holders, a transport medium for transporting the vessel holders between the components of the system, a work cell for processing, a storage module for empty vessel holders, wherein the storage module is connected to the transport medium, a robotic manipulator for engaging and/or disengaging the vessels with empty vessel holders, an empty vessel holder transfer unit for introducing empty vessel holders into or retrieving them from the storage module, and an empty vessel holder detection unit, including an empty vessel holder detector for discriminating between filled and empty vessel holders as well as a transfer initiator configured to initiate the introduction or re-introduction of an empty vessel holder detected in or on the transport medium into the storage module by the empty vessel holder transfer unit.

17 Claims, 14 Drawing Sheets

(51) Int. Cl.
*G01N 35/02* (2006.01)
*G01N 1/28* (2006.01)
*G01N 33/00* (2006.01)
B01L 9/06 (2006.01)
G01N 35/04 (2006.01)

(52) U.S. Cl.
CPC ......... *G01N 35/0099* (2013.01); *G01N 35/02* (2013.01); *B01L 9/06* (2013.01); *G01N 2035/0462* (2013.01); *G01N 2035/0465* (2013.01); *G01N 2035/0467* (2013.01); *G01N 2035/0491* (2013.01); *Y10T 436/2575* (2015.01)

(58) Field of Classification Search
CPC ........... G01N 2035/0491; G01N 33/00; G01N 35/0099; G01N 35/025; Y10T 436/2575
See application file for complete search history.

(56) References Cited

U.S. PATENT DOCUMENTS

| | | |
|---|---|---|
| 5,814,276 A | 9/1998 | Riggs |
| 2007/0134130 A1 | 6/2007 | Hutchins et al. |
| 2007/0274741 A1 | 11/2007 | Shiraishi et al. |
| 2009/0142844 A1 | 6/2009 | Le Comte |
| 2009/0191095 A1 | 7/2009 | Nakamura |
| 2010/0062480 A1 | 3/2010 | Graf et al. |
| 2010/0322822 A1 | 12/2010 | Fritchie et al. |
| 2011/0000763 A1 | 1/2011 | Kimura et al. |
| 2012/0177547 A1 | 7/2012 | Fukugaki et al. |
| 2014/0036276 A1 | 2/2014 | Gross et al. |
| 2014/0037517 A1* | 2/2014 | Takai ..................... B01L 9/06 422/562 |

\* cited by examiner

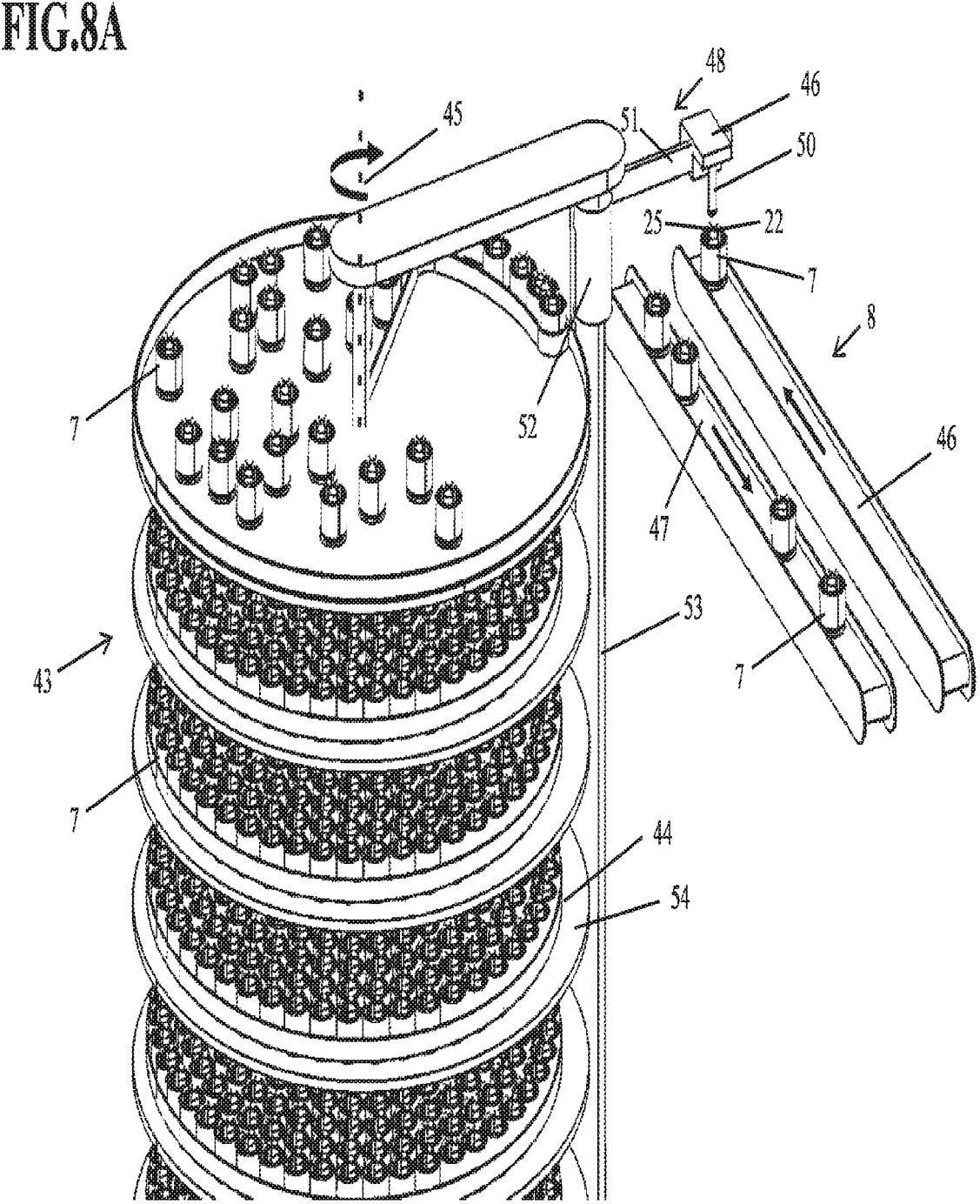

STORAGE AND SUPPLY FOR VESSEL HOLDERS

CROSS-REFERENCE TO RELATED APPLICATIONS

This application is a continuation of patent application Ser. No. 14/567,531, filed on Dec. 11, 2014, now U.S. Pat. No. 9,684,007, which is a continuation of EP 13198403.1, filed Dec. 19, 2013, which is hereby incorporated by reference.

BACKGROUND

The present disclosure generally relates to the field of processing biological samples for analytical purposes and, in particular, to an automated system and method for processing vessels containing the biological samples where the vessels are placed and moved while held in vessel holders.

The processing of biological material is of considerable significance for analytical purposes. Automated systems such as analyzers are commonly used in such processes. Devices are commercially available which typically require vessels such as test tubes or vials for biological samples and/or reagent liquids.

In order for the analyzer to conduct experiments on a biological sample, for example in a clinical laboratory, the vessel containing the sample usually needs to be supported by a vessel holder, which may be, for example, a rack for multiple vessels, or a holder for a single vessel.

In an analyzer, a vessel needs to be transported by a suitable transport medium, such as a conveyor, to the site of analysis or the respective preparative steps. For opening the vessel and manipulating the sample therein by robotic manipulators, the vessel needs to be maintained in a specific orientation. A vessel holder contributes to providing such conditions, for example, by establishing a connection between the vessel holder and the transport medium and maintaining the vessel in a proper position during manipulation of the sample in a work cell. Hence, an automated system needs to employ a sufficient quantity of vessel holders in order to ensure a proper workflow with regard to the vessels containing biological samples.

However, empty vessel holders are vessel holders in an idle mode, i.e. not holding a vessel, and the presence of too many of them can pose a significant burden on the components of a system and adversely affect the system's performance.

Firstly, empty vessel holders physically occupy space in the automated system. The transport medium should be available for the transport of vessel holders in an operative mode, i.e. holding vessels containing biological samples, such that they can be delivered to the respective components of the automated system. Any empty and thus idle vessel holder is therefore unnecessary and thus an undesired element in or on the transport medium.

Secondly, automated systems like analyzers mostly require controlling software running on a computer which, among other tasks, controls the transport of samples within the system. For this and other purposes, elements moving within the system are often frequently identified on their route. For instance, a vessel holder holding a vessel containing a biological sample needs to be identified upon arrival at an intersection, such that it may move in the correct direction and be transported to the appropriate station of the system, such as a work cell. As an example, an automated system may include one distinct work cell for each specific type of sample. Hence, a vessel holder holding a vessel with a blood sample would have to be identified as such upon arrival at an intersection in order to be correctly transported to the work cell for blood samples, whereas a vessel holder holding a vessel with a urine sample would have to be identified to be transported to another dedicated work cell. If empty vessel holders are also identified at each of the respective identification points, they are not transported to a dedicated work cell, but can remain in or on the transport medium and are thus repeatedly identified. Each of these unnecessary identification events creates data, which in sum may considerably slow down the computer system controlling the analyzer. This is especially the case since many systems involve the use of databases into which data collected during such identification events have to be entered and compared to stored data for identification and workflow direction.

The problems mentioned above are of particular significance in the case of medium- to high-throughput analysis, as often encountered in central clinical laboratories or blood banks. With an increasing number of samples to be analyzed within a certain period of time, the demand for vessel holders becomes accordingly higher, and the system needs to work as efficiently as possible.

SUMMARY

The shortcomings described above are addressed by the automated system described herein. The system includes a plurality of vessel holders that are used for holding and manipulating vessels containing biological samples. The vessel holders, with or without vessels, are moved within the system via a transport medium, for example, to a work cell for processing the vessels and thus, in most cases, also the biological samples contained therein. Further, the system includes a storage module where empty members of the plurality of vessel holders are stored. The storage module is connected to the transport medium via an empty vessel holder transfer unit facilitating introduction and retrieval of empty vessel holders. Since vessels have to be mated with empty vessel holders or retrieved from the vessel holders after they have been processed, the system also has a robotic manipulator carrying out these steps when needed. Being an automated system, the system described herein is controlled by a control unit.

The negative effects of empty, "idle" vessel holders circulating within the system, as described above, are mitigated by an empty vessel holder detection unit of the system described herein. This unit includes an empty vessel holder detector which discriminates between empty vessel holders and vessel holders holding a vessel. The unit also includes a transfer initiator that, based on the discrimination mentioned above, is responsible for initiating the transfer of the detected empty vessel holders to the storage module. Hence, empty vessel holders can be readily removed from the transport medium and do thus not burden the system by taking up space or computational capacities.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIGS. 8A-C illustrate the storage module as a rotatable silo according to an embodiment of the present disclosure.

DETAILED DESCRIPTION

Figure 1:
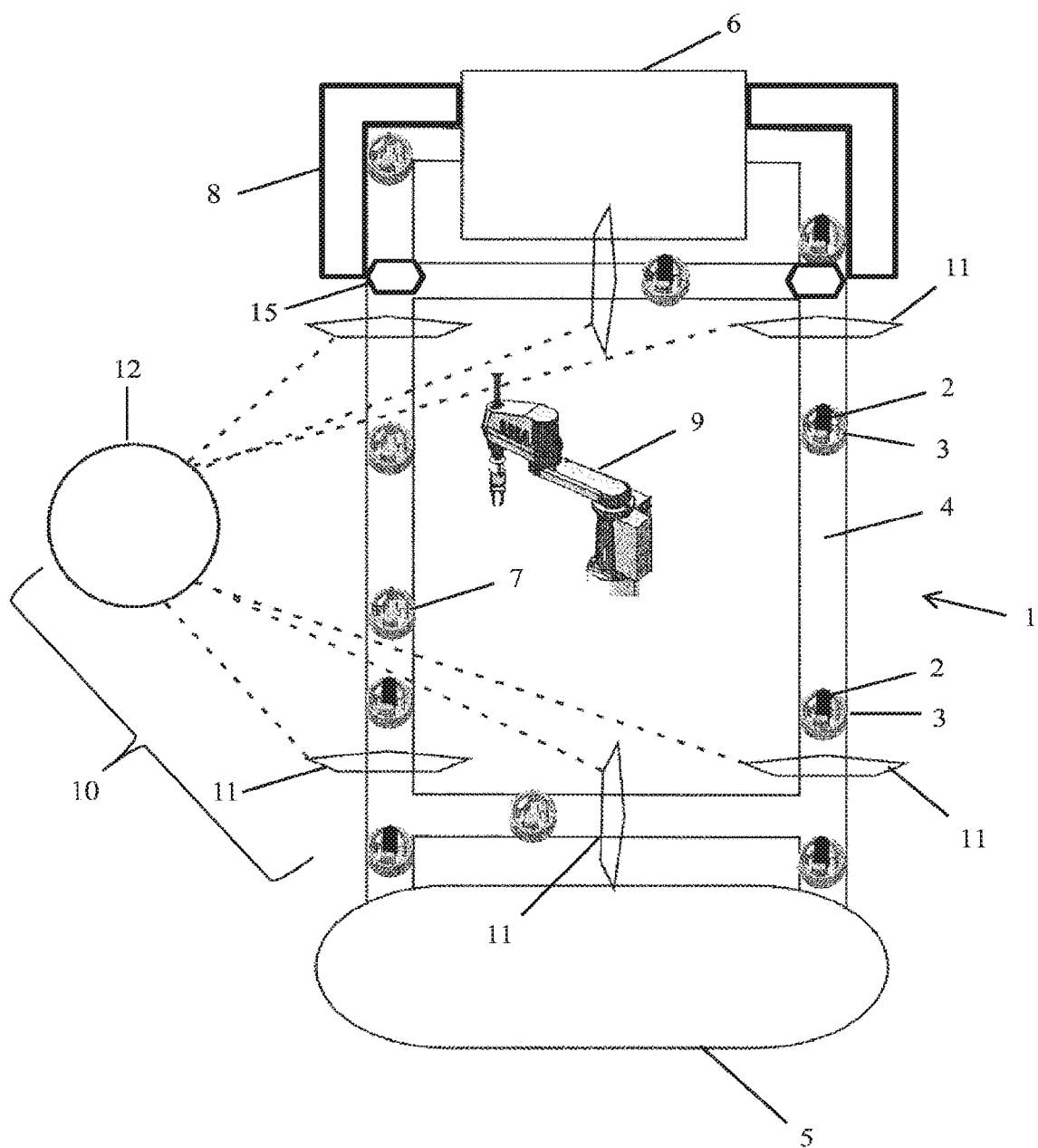
FIG. 1 illustrates schematic overview of the automated system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

An automated system for processing vessels containing biological samples is described. The automated system can comprise a plurality of vessel holders for the vessels containing biological samples, a transport medium for transporting the vessel holders within the automated system, a work cell for processing the vessels containing biological samples, and a storage module for empty members of the plurality of vessel holders. The storage module can be connected to the transport medium via an empty vessel holder transfer unit for retrieving empty vessel holders from the transport medium and introducing them into the storage module or retrieving empty vessel holders from the storage module and placing them in or on the transport medium. The automated system can further comprise a robotic manipulator for engaging and/or disengaging the vessels containing biological samples with the empty members of the plurality of vessel holders, a control unit for controlling the automated system, and an empty vessel holder detection unit for detecting empty vessel holders in or on the transport medium. The empty vessel holder detection unit can comprise an empty vessel holder detector for discriminating between filled and empty vessel holders, and a transfer initiator configured to initiate the introduction or re-introduction of an empty vessel holder detected in or on the transport medium into the storage module by the empty vessel holder transfer unit.

The automated system addresses a number of problems in the art. As discussed above, vessels containing biological samples usually require a holder in order to be introduced into and processed by an automated analytical system, for example in a clinical laboratory, and idle vessel holders can considerably slow down or otherwise impede the workflows performed on that system.

In contrast to other systems in the art, the automated system described herein can be configured to detect any potential empty vessel holders in or on the transport medium and remove them. In turn, the present automated system provides empty vessel holders to the transport medium whenever required in order to process vessels containing biological samples.

The automated system described herein can dispense empty vessel holders from a respective storage module when the holders are needed for operation, i.e. for being mated with specific vessels containing biological samples. This can already reduce the number of empty vessel holders in or on the transport medium as compared to systems where a maximum amount of empty vessel holders is circulating in the transport medium in order to ensure their availability for the respective vessels. Furthermore, the circumstance that the holders can be reintroduced into the storage module upon switching from operative to idle mode can abolish the need for the presence of excessive quantities of empty vessel holders in the automated system, which can also reduce the required footprint of the system.

By detecting any empty vessel holder circulating in the system in the idle mode and consequently removing it from the transport medium and storing it in the storage module, the automated system described herein can reduce the complexity of the related workflows, accelerate the respective procedure and render it more efficient.

As used herein, the term "vessel" can include, but is not limited to, tubes, or microwell plates, deepwell plates, or other types of multiwell plates. The inner walls of such vessels can be usually chemically inert such that they do not interfere with any reaction taking place within, or react with the biological sample stored therein. In some embodiments, the "vessel" can be a tube.

The term "biological sample" can refer to a material that may potentially contain an analyte of interest. The sample can be derived from any biological source, such as a physiological fluid, including blood, saliva, ocular lens fluid, cerebrospinal fluid, sweat, urine, semen, milk, ascites fluid, mucous, synovial fluid, peritoneal fluid, amniotic fluid, tissue, cells, or the like. The test sample can be pretreated prior to use, such as preparing plasma from blood, diluting viscous fluids, lysis or the like. Methods of treatment can involve filtration, distillation, concentration, inactivation of interfering components, and the addition of reagents. A biological sample may be used directly as obtained from the source or used following a pretreatment to modify the character of the sample. In some embodiments, the biological sample can be suspected to contain a certain antigen or nucleic acid.

As used herein, the term "vessel holder" can mean a holder for a vessel containing a biological sample. As outlined above, a vessel holder can be used in many automated systems in order to transport the vessel using the transport medium, or to maintain the vessel in a proper position during manipulation of the sample in a work cell. In some embodiments, the vessel holder can be adapted to constrain one or more vessels in a generally vertical and concentric orientation. The vessel holder can be, in some embodiments, a holder for a single vessel such as a tube. In some embodiments, the vessel holder can be cylindrical, in some embodiments, puck-shaped. The vessel holder can also be a rack for multiple vessels such as two, three, four or more vessels. The vessel holder can, for example, be a socket into which the bottom of a tube can be reversibly placed, such as by pressure-fitting, snap-fitting or screw-fitting, or the like. The vessel holder can also embrace a larger portion or even all of the tube, but in some embodiments, the upper end of the tube can be left accessible for manipulation, detection or reading of a label or identification tag in the respective work cell or cells or in or on a transport medium. In some embodiments, the vessel holder itself can include an identification tag such as a barcode, or an RFID tag, or the like.

A "transport medium" can be the system component by which vessel holders can be moved within the automated system. The transport medium may, for example, include or be a conveyor such as a band conveyor, a roller conveyor, a pneumatic conveyor, a vibrating conveyor, a vertical conveyor such as a lift, a spiral conveyor, or the like. The transport medium can also include or be a surface with an integrated transport mechanism such as a hover cushion or a magnetic surface. In other embodiments, the transport medium can include or be a rail system.

A "work cell" can be a module within an analytical system that can perform one or more functions. For example, a work cell can assist users with processing vessels containing biological samples, and thus ultimately the samples themselves. "Processing" a sample can mean manipulation of a sample for analytical or pre- or post-analytical purposes. The term processing may thus include detection, such as qualitative and/or quantitative evaluation of samples for diagnostic purposes, and/or sorting and/or preparation of samples before detection, or storing and/or disposal of samples after detection. In particular, a work cell may be related to analytical and/or to pre-analytical and/or to post-analytical sample processing steps. Work cells may be connected to each other and depend at least in part on each other. They may be each carrying out one or more dedicated tasks of a sample processing workflow, which may be a prerequisite before proceeding to another work cell. Alternatively, work cells may work independently from each other, such as each carrying out one or more separate tasks like different types of analysis on the same or different samples. In general, a work cell may include units for loading and/or unloading and/or transporting and/or storing sample tubes or racks holding sample tubes or multiwell plates, units for loading and/or unloading and/or transporting and/or storing reagent containers or cassettes, units for loading and/or unloading and/or transporting and/or storing and/or washing reagent vessels, for example, cuvettes, units for loading and/or unloading and/or transporting and/or storing pipette tips or tip racks. It may include identification units having sensors, e.g., barcode or RFID readers. It may also include wash stations for washing pipette tips or needles or reaction vessels, e.g., cuvettes, mixing paddles, or the like. The work-cell may further include one or more incubation units for maintaining sample/reagent mixtures at a certain temperature during reaction. The work cell may include a thermocycler for subjecting a sample to repeated temperature cycles and/or varying temperature conditions. Such a thermocycler may be particularly useful in the case of an analytical work cell, such as for conducting a polymerase chain reaction.

A "storage module" can be a device that stores empty vessel holders. The storage module can have different shapes, sizes and designs. It can be connected to the transport medium via an "empty vessel holder transfer unit" (see infra) in a manner that the empty vessel holders can be introduced into and retrieved from the storage module via the empty vessel holder transfer unit. Within the storage module, there can be, in some embodiments, also a transport system, which may be a continuation of the transport medium of the automated system described herein. For instance, a band conveyor serving as a transport medium may extend through the storage module, and can be manipulated to either introduce empty vessel holders into the storage module or to retrieve them from the storage module. In other embodiments, the storage module may not include such a transport system, but rather be a bulk container in which the empty vessel holders can be stored in an unstructured manner. Further in some embodiments, the empty vessel holders can be stored in the storage module in a predefined geometrical arrangement. For instance, the empty vessel holders may be stacked vertically to form multiple layers, and the storage module may contain one or more of such stacks. The stacks may be formed on a socket located at the bottom of the storage module, and/or they may be held in tube-like structures such as tubes made from glass, plastic or metal. The empty vessel holders may in other embodiments also be arranged in spirals extending both horizontally and vertically, thus providing efficient usage of the space available within the storage module. Other non-limiting embodiments are described throughout the Description and the Examples and Figures herein.

The "empty vessel holder transfer unit" can perform the introduction of empty vessel holders into the storage module or their retrieval therefrom by establishing a connection between the storage module and the transport medium. For this purpose, the "empty vessel holder transfer unit" may include or be an actuator for guiding empty vessel holders from the transport medium into the storage module or for directing them from inside the storage module towards the transport medium. In some embodiments, the empty vessel holder detection unit can include a band conveyor as a connection between storage module and transport medium. In other embodiments, the transfer unit can include or be two or more conveyor bands, such as one band for introducing and one band for retrieving empty vessel holders. In other embodiments, the transfer unit can include one or more rails. There may be a single conveyor band, rail, or other suitable connection element which can be moveable in horizontal and/or vertical direction. In other embodiments, there may be two or more conveyor bands, rails, or other suitable connection elements, wherein either one or more of these connection elements can be moveable in horizontal and/or vertical direction. This may, for instance, be of particular advantage in embodiments involving a storage module with a substantial extension in vertical direction, i.e., including one or more stacks of empty vessel holders that may be arranged in multiple levels. Thus, a vertically moveable connecting element such as a robotic manipulator moveable in x, y, and z direction may retrieve empty vessel holders from the different levels or introduce them therein.

In other embodiments, there may be a magnetic surface as a transport medium on which the vessel holders can be moved by dynamic magnetic fields. In such embodiments, the above-mentioned connection may be established by simply providing an entry and an exit for the empty vessel holders in the storage module, or a single interface serving as both entry and exit. For guiding the empty vessel holders in the appropriate direction, the empty vessel holder transfer unit, in some embodiments, can include barriers, rails, deflectors, switch points or other appropriate structures. In embodiments where the transport medium does not include predefined paths such as bands or rails, for example, in the case of a magnetic surface, the empty vessel holder transfer unit may essentially be the entry and/or exit of the storage module for the empty vessel holders, since the magnetic field or fields may direct the empty vessel holders towards and into or out of and away from the storage module without any further substantial mechanical intervention.

A "robotic manipulator" can be an automated manipulator configured to manipulate vessel holders and/or vessels. It can be capable of engaging and/or disengaging the vessels containing the biological samples with the empty members of the plurality of vessel holders. In some embodiments, the robotic manipulator can be a gripper that can pick up a vessel containing a biological sample at a certain point within the automated system described herein and engage it to the vessel holder or disengage it therefrom after processing in the work cell. In some embodiments, it can be moved laterally (along an x- and or y-axis) and vertically (along a z-axis). In some embodiments, the robotic manipulator can be moved within a part or all of the automated system. In order to be moveable, the robotic manipulator may be flexibly suspended and/or include a flexible robotic arm. For instance, movement may be facilitated by a rotatable robotic arm fixed to the bottom or the ceiling of the automated system described herein. Alternatively or additionally, movement may be achieved by a telescope arm. Also, the robotic manipulator may include a bipartite robotic arm rotatable at its base at the bottom of the automated system, wherein the two parts of the arm can be attached to each other via a hinge or another type of joint. By combined movement of the hinge and rotation of the arm at its base, the robotic manipulator may be moveable in all directions. In order to handle vessels and/or vessel holders, it can, for example, include gripper arms. In such embodiments, the robotic manipulator can be a gripper. Alternatively or additionally, the robotic manipulator can include means to apply a vacuum or at least negative pressure. Such a structure can, for instance, be or include a vacuum cup. In further embodiments, the robotic manipulator can include a robotic arm or a comparable mechanic structure for holding the vessel holder in a specific position while the vessel is being engaged to it, and/or holding the vessel holder down while the vessel is being disengaged from the vessel holder. In some embodiments, more than one robotic manipulator can be used. For instance, two, three or four robotic manipulators may act simultaneously or at different times within the automated system.

The "empty vessel holder detection unit", as used herein, can be a unit that can discern empty vessel holders from vessel holders holding a vessel and can initiate the transfer of empty vessel holders to the storage module. The empty vessel holder detection unit can include an "empty vessel holder detector" and a "transfer initiator". The "empty vessel holder detector" can be configured to discriminate between empty vessel holders and vessel holders holding a vessel. The empty vessel holder detector may include suitable detection technologies such as the ones used in the embodiments described herein. Further, the empty vessel holder detector can include at least one detecting element. Such detecting elements may be within or in close spatial relation to the transport medium, such that empty vessels can pass through such an element or can otherwise be detected by the latter. In some embodiments, optical discrimination based on algorithms for visual recognition may be used. Hence, the empty vessel holder detector can monitor the presence of any empty vessel holder in some embodiments circulating in or on the transport medium. The "transfer initiator" can be configured to initiate further action upon detection of an empty vessel holder in or on the transport medium by the empty vessel holder detector. More precisely, the transfer initiator can initiate the introduction or re-introduction of an empty vessel holder into the storage module by the empty vessel holder transfer unit. In some embodiments, both detection and transfer initiation may be accomplished by mechanical means without computation. An empty vessel holder may be detected based on its shape fitting through, for example, a gate which may, in turn, not allow vessel holders holding a vessel to pass through. In such an embodiment, transfer initiation may also be accomplished by such a mechanism, for example, the empty vessel holders fitting through the gate may be directly forwarded to the storage module.

In some embodiments of the automated system described herein, the empty vessel holder detection unit can comprise a programmable logic controller configured to discriminate between empty and filled vessel holders and/or to direct an empty vessel holder detected in or on the transport medium to the storage module. Typically, such direction can be along the shortest possible route to the storage module, but it can be along a path that least interferes with transport of vessel holders containing a vessel.

A programmable logic controller may include algorithms for discriminating between empty vessel holders and vessel holders holding a vessel based on data provided by the empty vessel holder detector. For instance, the empty vessel holder may include an optical system such as a camera providing images to the transfer unit. The latter may, based on these images, determine whether or not the respective vessel holder is empty and can thus be sent to the storage module. In such embodiments, the transfer unit may include a comparison library of imaging data relating to vessel holders with and without vessels. Additionally or alternatively, the transfer unit may comprise a robotic manipulator such as a robotic gripper with, for example, gripper arms or a vacuum cup, for retrieving detected empty vessel holders from the transport medium and transferring them to and, in some embodiments, also introducing them into the storage module. In the latter case, the robotic gripper can also serve as an empty vessel holder transfer unit. When combining such a robotic manipulator with an optical system including, for example, a camera, empty vessel holders in or on the transport medium may be imaged, detected by the programmable logic controller and subsequently removed from the transport medium and transferred to the storage module by the robotic gripper.

In some embodiments, the programmable logic controller can flag the detected empty vessel holder for the empty vessel holder transfer unit to retrieve the detected empty vessel holder from the transport medium and introduce the detected empty vessel holder into the storage module.

Such flagging may be achieved in various ways, only some of which can be illustrated in the following. In general, the flagging can ultimately lead to the introduction of the flagged empty vessel holders into the storage module. An empty vessel holder may be flagged by the programmable logic controller in a mechanical manner. For instance, each vessel holder may include a mechanical indicator such as a flag that has two possible positions. A horizontal position may label the vessel holder as empty, while a vertical position may indicate that the vessel holder holds a vessel. In such an embodiment, the programmable logic controller may include a mechanical arm for adjusting the position of the flag. Alternatively or additionally, an empty vessel holder may be flagged in an electronic manner. For example, if the empty vessel holder detector comprises a camera, empty vessel holders may in some embodiments not only be detected, but may be flagged for the robotic gripper to be transferred to the storage module. In cases where the camera is included on the robotic gripper, the camera may track an empty vessel holder flagged by the programmable logic controller and retrieve it from the transport medium with visual guidance provided by the camera. Alternatively, as described herein, the transfer unit may include an RFID writer for adding the information to an RFID tag on a vessel holder that the respective vessel holder is empty and needs to be transferred to the storage module.

The automated system described herein can further comprise a control unit for controlling the automated system. Such a "control unit" can control the automated system in a way that the necessary steps for the assay protocols can be conducted by the automated system. That can mean the control unit may, for example, instruct the automated system to conduct certain pipetting steps to mix the sample with reagents or the control unit can control the automated system to incubate the sample mixtures for a certain time and so on. The control unit may receive information from a data management unit regarding which test has to be done with a certain sample and based thereon may determine the steps the automated system has to perform. In certain embodiments, the control unit may be integral with the data management unit or may be embodied by a common hardware. The control unit may, for instance, be embodied as a programmable logic controller running a computer-readable program provided with instructions to perform operations in accordance with a process operation plan. The control unit may be set up to control, for example, any one or more of the following operations: loading and/or wasting and/or washing of cuvettes and/or pipette tips, moving and/or opening of sample tubes and reagent cassettes, pipetting of samples and/or reagents, mixing of samples and/or reagents, washing pipetting needles or tips, washing mixing paddles, controlling of the light source, e.g., selection of the wavelength, controlling the detector, collecting/comparing/assessing measurement data, moving the cuvette holder to bring a new cuvette in the optical path or bringing a new cuvette into the cuvette holder after each measurement, or the like. In particular, the control unit may include a scheduler, for executing a sequence of steps within a predefined cycle time. The control unit may further determine the order of samples to be measured according to the assay type, urgency, and the like.

In some embodiments, the automated system described herein can further comprise a data management unit. A "data management unit" can be a computing unit for storing and managing data. This may involve data relating to the biological sample to be processed by the automated system, or data about the quantity of empty vessel holders available in the storage module, or data relating to the steps to be carried out within a work cell. The data management unit may be connected to an LIS (laboratory information system) and/or an HIS (hospital information system). The data management unit (DMU) can be a unit within or co-located with the automated system. It may be part of the control unit. Alternatively, the DMU may be a unit remotely located from the analyzer. For instance, it may be embodied in a computer connected via a network to the automated system.

Automated System for Processing Vessels

FIG. 1 shows a scheme of the automated system (1) described herein. The transport medium (4) can be a linear, two-dimensional structure and may, in this embodiment, be a band-conveyor on which a plurality of vessel holders (3) can be circulating. In the embodiment shown, the vessel holders (3) can be single-vessel holders. A part of these vessel holders (3) can hold a vessel (2) containing a biological sample. Other vessel holders (3) may not hold a vessel (2) and can thus be empty vessel holders (7). A robotic manipulator (9) for engaging and/or disengaging the vessels (2) containing biological samples with the empty members (7) of the plurality of vessel holders (3), in one embodiment, a robotic gripper, can be located in the center of the circuit comprised by the transport medium (4). Empty members (7) of the plurality of vessel holders (3) can be stored in the storage module (6) and retrieved therefrom and placed on the transport medium (4) via the empty vessel holder transfer unit (8) when needed. When the gripper (9) engages a vessel (2) containing a biological sample to an empty vessel holder (7), the resulting vessel holder (3) holding a vessel (2) containing a biological sample can be transported further via the transport medium (4) to the work cell (5) for processing of the vessel (2) containing a biological sample and thus usually ultimately the sample itself. After processing, the vessel holder (3) holding the vessel containing the biological sample (2) can be moved out of and away from the work cell (5) via the transport medium (4). The vessel (2) can be then disengaged from the vessel holder (3) by the robotic manipulator (9). The resulting empty vessel holder (7) which can still be circulating on the conveyor (4) can then be detected by an element of the empty vessel holder detector (11) which can be part of the empty vessel holder detection unit (10), and the transfer initiator (12) can also be a part of the empty vessel holder detection unit (10) then can initiate the introduction of the respective empty vessel holder (7) into the storage module (6) via the empty vessel holder transfer unit (8). The latter, in one embodiment, can include switches (15) at the junctions connecting transport medium (4) and empty vessel holder transfer unit (8). These switches (15) can be activated by the transfer initiator (12) after detection of an empty vessel holder (7) on the transport medium (4) by the empty vessel holder detector (11), with the appropriate timing for the respective vessel holder (7) to be directed into the storage nodule (6) instead of circulating further on the transport medium (4).

Empty Vessel Holder Detection Unit

For the purpose of detecting empty vessel holders in or on the transport medium, the empty vessel holder detector can exploit a variety of technologies, either within one or multiple different embodiments.

Thus, in some embodiments of the automated system described herein, the empty vessel holder detector can comprise a mechanical, electrical, electromechanical, electromagnetic, or optical sensor.

A mechanical sensor can be a detection system based on mechanical properties of the vessel holders to be detected. For instance, an empty vessel holder may be detected due to its smaller dimensions as compared to a vessel holder holding a vessel. For instance, a gate belonging to the empty vessel holder may only allow empty vessel holders to pass it. In such an embodiment, vessel holders passing the gate can be detected as empty vessel holders. For example, empty vessel holders may move a lever included by the gate, and the lever may mechanically trigger a counter with which it may be physically connected.

Another embodiment of a mechanical detection approach can involve the automated separation of empty vessel holders and vessel holders holding vessels and can comprise a mechanical switch.

In some embodiments of the automated system described herein, the empty vessel holder detector can comprise a mechanical barrier located in a position relative to a vessel holder circulating in or on the transport medium, wherein the first position can intersect the track of a vessel if present in the vessel holder, such that a vessel and its vessel holder can be deviated by the mechanical barrier relative to an empty vessel holder circulating in or on the transport medium.

Figure 2:
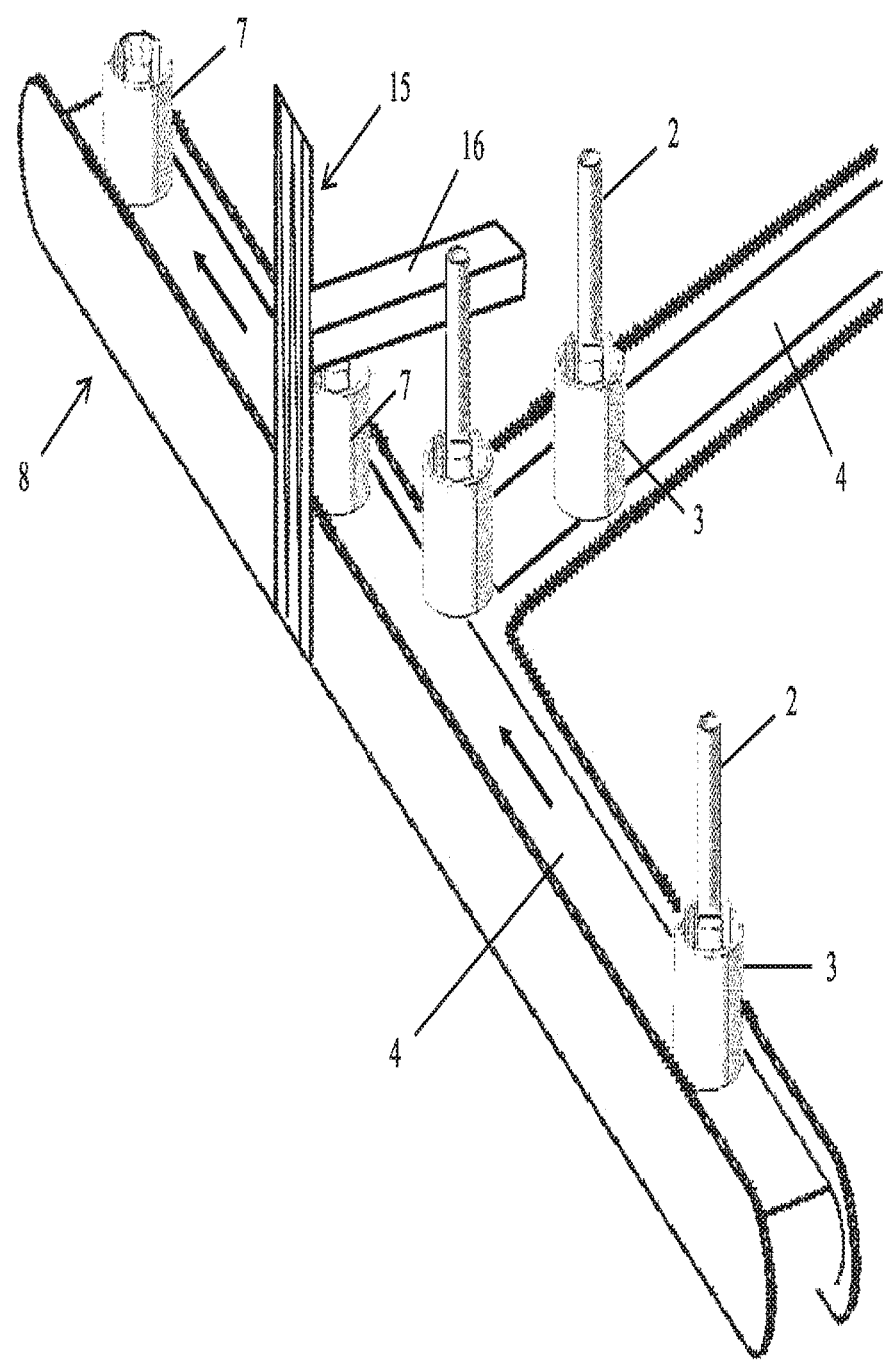
FIG. 2 illustrates the empty vessel holder detection unit comprising a switch according to an embodiment of the present disclosure.

In other words, an empty vessel holder may not be deviated and can continue on its original track, while a vessel holder holding a vessel containing a biological sample can be directed into a different direction. The empty vessel holders may thus be directed into the storage module, while the redirected vessel holders holding a vessel may keep circulating in or on the transport medium. Such an embodiment is depicted in FIG. 2. In this embodiment, the empty members (7) of the plurality of vessel holders (3) can be automatically separated from the vessel holders (3) holding vessels (2) containing biological samples. The empty vessel holder transfer unit (8) and the transport medium (4) can be connected to each other via a switch (15) that can direct the vessel holders (3) holding vessels (2) in such a manner that they can remain on the transport medium (4) which is here depicted as a band-conveyor. The arrows along the band indicate the direction in which it moves. Vessel holders (3) holding a vessel (2) containing a biological sample can collide with a mechanical barrier (16) being part of the switch (15), because the upper portion of the depicted vessel (2) can protrude from the vessel holder (3) at a sufficient length to be intersected on its track on the transport medium (4) by the mechanical barrier (16) arranged at a height appropriate for this purpose. The respective vessel holders (3) can then be guided along the mechanical barrier (16) to turn towards the continuation of the transport medium (4). Hence, in this embodiment, the mechanical barrier (16) may not be positioned higher than the vessel (2) can extend in vertical direction, nor may it be positioned at such low height that it can intersect the track of the vessel holder (3) itself. In the former case, no vessel holder (3) can be deviated at all and thus no separation can take place, and in the latter case both vessel holders (3) holding a vessel (2) containing a biological sample and empty members (7) of the plurality of vessel holders (3) can collide with the mechanical barrier (16) and thus be directed to remain circulating on the transport medium (4). In contrast, the depicted embodiment can allow the undisturbed passage of empty members (7) of the plurality of vessel holders (3) through or past the switch (15) by passing below the mechanical barrier (16), such that they can continue on the empty vessel holder transfer unit (8) which in this embodiment can essentially be a continuation of the band-conveyor leading to the storage module (6). In the depicted embodiment, detection of the empty members (7) of the plurality of vessel holders (3) can be achieved by the specific construction of the switch (15) which in this case therefore can serve as the empty vessel holder detection unit (10). The mechanical barrier (16) can thus discriminate between filled and empty (7) vessel holders (3) by collision with the protruding vessels (3) if present and thereby can serve as an empty vessel holder detector (11). In order to prevent the vessel holders (3) containing vessels (2) from falling over upon collision with the mechanical barrier (16), various solutions can be possible. For instance, the vessel holders (3) may be of sufficient weight to ensure a stable position of the vessel holder (3) even if the vessel (2) collides with the barrier (16) and therefore a leverage force can be exerted on the combination of vessel (2) and holder (3). Alternatively or additionally, the mechanical barrier (16) may be arranged at a wider angle towards the part of the transport medium (4) from which the vessel holders (3) arrive at the barrier (16). In such embodiments, the leverage force can be smaller since a larger part of the vessel (2)/vessel holder (3) combination's kinetic force can act upon the barrier (16) and thus vice versa. Instead, the vessel (2) with its holder (3) can be more smoothly guided along the barrier (16) towards the respective branch of the transport medium (4). Also, the vessel holders (3) may be attached to the transport medium (4) by, for example, magnetism, or mechanical connections such as hooks included by the vessel holders (3) interacting with rails of the transport medium, or the like.

An electrical sensor can be based on electrical signals indicating an empty or a filled vessel holder. An electromechanical sensor can involve both mechanical and electrical principles, such as the conversion of a mechanical displacement into an electrical signal or vice versa. An electromagnetic sensor can be based on electromagnetic principles, for example, the induction of a current by changing a magnetic field.

An optical sensor can be based on optical principles for recognition of an empty vessel holder. For instance, an optical sensor may include a camera.

In some embodiments the automated system described herein may include structures for detecting both the vessel holder and the vessel comprising the biological sample, if present. In such embodiments, the presence of a vessel or a vessel holder can evoke a detectable signal in the empty vessel holder detector of the empty vessel holder detection unit. The signal may be a mechanical, electrical, electromechanical, electromagnetic, or optical signal. When the empty vessel holder detector in a measurement detects a signal for a vessel holder as well as a signal for a vessel, then the respective vessel holder can be determined to hold a vessel. If, on the other hand, the empty vessel holder detector detects a signal for a vessel holder, but not for a vessel, then the presence of an empty vessel holder can be indicated. In such a case, the transfer initiator of the empty vessel holder detection unit can initiate the introduction of the empty vessel holder into the storage module by the empty vessel holder transfer unit.

In one such embodiment, the empty vessel holder detector can comprise a first indicator located in a first position and a second indicator located in a second position relative to a vessel holder circulating in or on the transport medium, wherein the first position can intersect the track of the vessel holder and the second position can intersect the track of a vessel if present in the vessel holder.

For instance, the vessel holder may be a puck for holding a single vessel, and the vessel may be placed onto or into the puck from above, such that at least a part of the vessel can extend above the upper limit of the puck. In such case, the first indicator may be located below the second indicator, such that the first indicator can be contacted by the puck and the second indicator can be contacted by the part of the vessel exceeding the upper limit of the puck. In the absence of a vessel, only the first indicator can be contacted and, thus, a signal can be generated only for the puck, indicating an empty puck.

An "indicator", as referred to herein, can be any suitable structure for interacting with a vessel or vessel holder with the aim of detection. It may include tangible objects, such as a gate or a barrier that detects the presence of a vessel or a vessel holder upon physical contact with the vessel. Thus, in some embodiments, the indicators of the automated system described herein can be mechanical flaps.

A non-limiting example of such an embodiment is described in the following. In general, mechanical flaps can have two opposite ends, one of which can be fixed and the other one can be flexible. The fixed end may be held in a position by being mounted to a holder, while the flexible end can be moved upon contact with a vessel or vessel holder, thus being or creating a signal detectable by the empty vessel holder detector. In some embodiments, the flap may be rectangularly mounted to a post extending vertically from the bottom of the automated system. The mechanical flap may be subject to a reset force with respect to its flexible end. For instance, the flap may be made of thin, flexible plastic, which can be moved away by a vessel or vessel holder upon physical contact, such that the vessel or vessel holder can pass and move ahead in or on the transport medium. After the vessel or vessel holder has passed, the flexible end may move back to its original position due to the reset force mentioned above and thus be in the proper position to be contacted by the next vessel or vessel holder. Alternatively, the flap may be made of a rigid material, but be able to move away with its flexible end upon physical contact with a vessel or vessel holder by means of a flexible mount. For instance, the flap may be mounted at its fixed end to the holder, such as a post as described above, via a hinge. The hinge may be subject to a reset force e.g., by a spring mechanism or it may be moved back into its original position by an actuator. The mechanical flap may also be mounted above the track of the vessels and vessel holders, for example, in a manner that the flexible end of the flap is contacted by the vessel if present in the vessel holder. Other embodiments with such mechanical flaps can be possible as known by the person skilled in the art. For instance, electromechanical principles may be exploited. In the embodiment described in the context of mechanical flaps, these flaps may trigger an electrical signal based on current or voltage, or another type of electrical signal. Alternatively or additionally, an indicator may include optical, magnetic or electromagnetic elements.

In some embodiments, the indicators of the automated system described herein can be photoelectric barriers. "Photoelectric barriers", as known in the art, can be barriers formed by radiation such as light. Breaking such a barrier can cause a specific stop signal, indicating the passage of a vessel or a vessel holder according to which barrier was broken. Thus, empty vessel holders can be discriminated from vessel holders holding a vessel. Photoelectric barriers can usually be supplied as a pair with a transmitter and receiver. The transmitter may project an array of parallel light beams such as infrared light beams to the receiver which may include a photoelectric cell. The receiver may be designed to only accept the specific light emitted by its dedicated transmitter.

If a vessel or a vessel holder breaks a photoelectric barrier, the respective stop signal can be indicative of the presence of a vessel or a vessel holder, leading to their detection by the empty vessel holder detector. In such embodiments, there may be two photoelectric barriers, one being broken by the vessel if present in the vessel holder, and the other being broken by the respective vessel holder. If only the barrier for the vessel holder is broken, then the presence of an empty vessel holder can be indicated. If both barriers are broken, then the presence of a vessel holder containing a vessel can be indicated.

Figure 3:
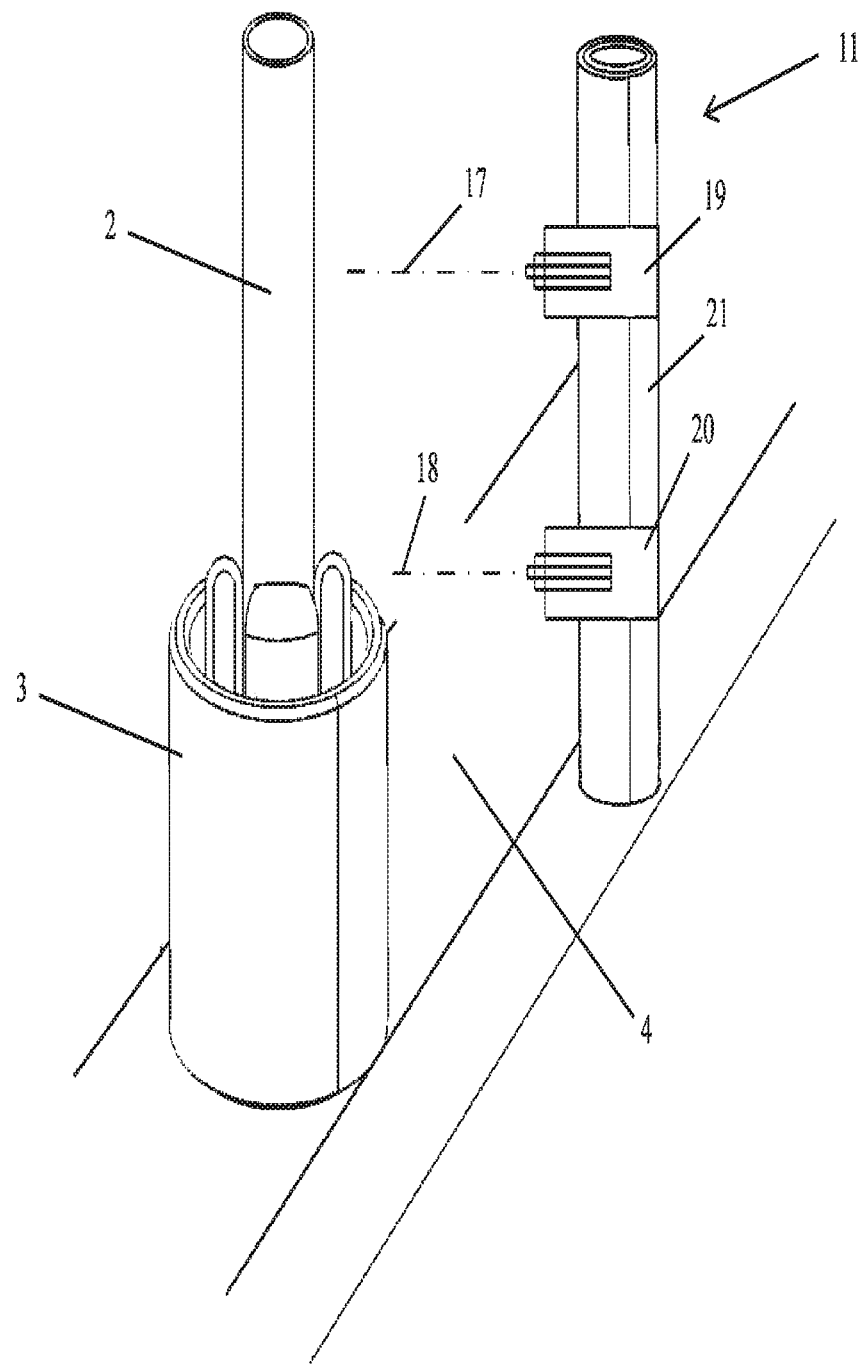
FIG. 3 illustrates the interaction of a vessel holder holding a vessel containing a biological sample with photoelectric barriers comprised by the empty vessel holder detector of the empty vessel holder detection unit according to an embodiment of the present disclosure.

A corresponding embodiment is depicted in FIG. 3. In this embodiment, the empty vessel holder detector (11) can include two photoelectric barriers (17, 18), an upper (17) and a lower (18) one, each generated by a distinct dedicated light source (19, 20), the latter being mounted on a pin-shaped holder (21). The light sources (19, 20) may generate a light barrier, for instance, of infrared light as a photoelectric barrier (17, 18). The light sources (19, 20) may also be lasers. Breaking one of the barriers (17, 18) can cause a signal specific for the upper or lower barrier (17 or 18) which can be detected by the empty vessel holder detection unit (10) via the empty vessel holder detector (11). In the depicted embodiment, a vessel holder (3) holding a vessel (2) containing a biological sample can be moved on the transport medium (4), in this embodiment a band-conveyor. The moving direction is indicated by an arrow. As in the embodiments shown above, the upper portion of the vessel (2) can protrude from the vessel holder (3) and thus can inevitably break the upper photoelectric barrier (17) which can be arranged at an appropriate height in order not to interfere with the vessel holder (3) itself. Thus, it can be avoided that empty vessel holders (7) also break the upper barrier (17). Instead, vessel holders (3) can break the lower barrier (18) when passing it and can create a signal specific for a vessel holder (3). If both the upper (17) and the lower (18) barriers are broken at the same time, then the empty vessel holder detector (11) can detect a vessel holder (3) holding a vessel (2) containing a biological sample. If only a signal caused by breaking the lower barrier (18) is detected, then the empty vessel holder detector (11) can detect an empty vessel holder (7). Based on this principle, the empty vessel holder detector (11) of the empty vessel holder detection unit (10) can achieve discrimination of vessel holders (3) holding a vessel (2) containing a biological sample and empty members (7) of the plurality of vessel holders (3). In other embodiments, the same principle can be realized with mechanical flaps instead of photoelectric barriers (17, 18).

Other embodiments of indicators can exploit different physical properties, such as gravimetric measurements. In such cases, the empty vessel holder detector of the automated system can comprise a weighing system. Such a weighing system may be integrated in the transport medium. For instance, in embodiments where the transport medium is a band-conveyor, the weighing system may be a part of the band-conveyor and located underneath the band. The measured value may, for instance, by comparison to data stored in a data management unit, be attributed to either an empty vessel holder or a vessel holder holding a vessel containing a biological sample, since the latter can exhibit a higher weight. Such discrimination may be carried out by a programmable logic controller included in the empty vessel holder detection unit.

Figure 4:
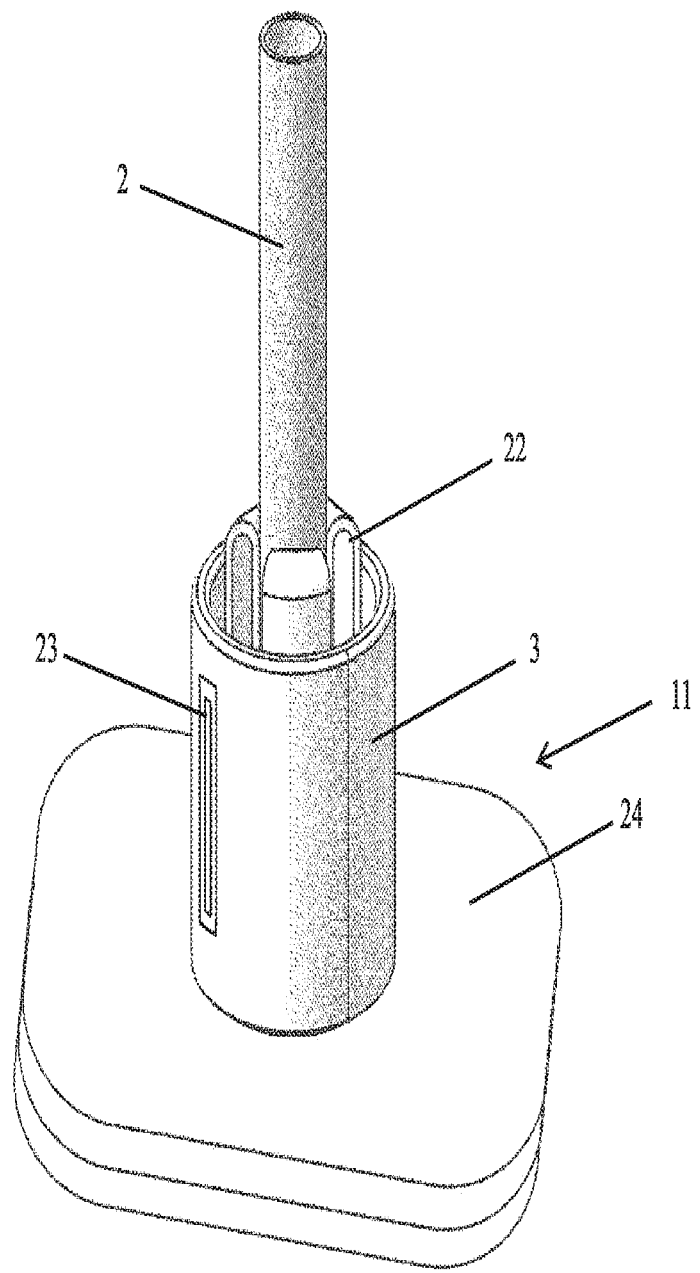
FIG. 4 illustrates the empty vessel holder detector of the empty vessel holder detection unit comprises a weighing system according to an embodiment of the present disclosure.

FIG. 4 depicts a part of the empty vessel holder detector (11) of the empty vessel holder detection unit (10) in an embodiment where the empty vessel holder detector (11) can include a weighing system (24). The weighing system (24) may be a balance which may be integrated in the transport medium (4). Alternatively, the weighing system (4) may be placed in close vicinity to the transport medium (4), for example, next to a band conveyor constituting the transport medium (4). In the latter case, the vessel holder (3) may be retrieved from the transport medium (4) and placed on the weighing system (24) by a quick and simple mechanism. For instance, vessel holders (3) passing by a weighing station including the weighing system (24) located next to a band-conveyor constituting the transport medium (4) may be routinely retrieved from the conveyor by a rotating disc. The retrieval may be effected by a cut-out in the disc arranged to receive a vessel holder (3). By rotation of the disc, the vessel holder (3) may be placed on the weighing system (24) next to the conveyor, and returned onto the conveyor after weighing and determining whether the vessel holder (3) holds a vessel (2) or whether it is an empty member (7) of the plurality of vessel holders (3). Alternatively, an empty vessel holder (7) detected by the weighing system (24) by determination of its lower weight may be placed on a second conveyor, or a shortcut to the storage module (6) so it can be introduced without much further delay. For this purpose, the rotating disc may place the empty vessel holder (7) directly from the weighing system (24) on the shortcut by rotation to a third position different from the weighing system (24) and the transport medium (4).

In another embodiment, the weighing system (24) may be placed underneath a conveyor band serving as the transport medium (4) at a switch point. According to the measured gravimetric value, the empty vessel holder detector (11) of the empty vessel holder detection unit (10) can discriminate between vessel holders (3) holding a vessel (2) containing a biological sample and empty members (7) of the plurality of vessel holders (3). The transfer initiator (12) of the empty vessel holder detection unit (10), which may in this case be or include a programmable logic controller, may then adjust the switch so as to direct the respective vessel holder (3) either to the storage module (6) if the vessel holder (3) is empty (7), or to remain on the transport medium (4) if the vessel holder (3) holds a vessel (2) containing a biological sample. In some embodiments, the desired direction of the respective vessel holders may be achieved by an identification tag (23).

In some embodiments of the automated system described herein, each vessel holder can comprise an identification tag for detection by the empty vessel holder detection unit. In some embodiments, the identification tag can be a barcode or an RFID tag.

A "barcode", as known to the skilled person, can be an optical machine-readable representation of data relating to the object to which it is attached, such as a vessel holder. Barcodes may systematically represent data by varying the widths and spacing of parallel lines, and may be referred to as linear or one-dimensional (1D). Alternatively, they may include rectangles, dots, hexagons and other geometric patterns in two dimensions (2D). Although 2D systems use a variety of symbols, they are generally referred to as barcodes as well. Barcodes may be scanned by special optical scanners called barcode readers.

"RFID" stands for radio-frequency identification and can mean the wireless non-contact use of radio-frequency electromagnetic fields to transfer data, for the purposes of automatically identifying and tracking tags attached to objects. The tags can contain electronically stored information. Some tags can be powered by magnetic fields (electromagnetic induction). Others can use a local power source such as a battery. Unlike a bar code, the tag may not necessarily need to be within line of sight of the reader and may be embedded in the tracked object. Hence, an RFID tag may enable the empty vessel holder detector to receive a signal from a vessel holder even from a certain distance to the latter. Consequently, an RFID-based empty vessel holder detector and its elements may not necessarily be co-located with the transport medium but may be located elsewhere in the automated system. Another advantage of RFID-based detection can be its flexibility. Microchips in RFID tags can be read-write, read-only or "write once, read many" (WORM). With read-write chips, information may be added to the tag or it may be written over existing information when the tag is within range of a reader.

In the case of read-write chips, the information stored on an RFID tag may be modified by components of the automated system described herein. If, for example, a vessel is disengaged from a vessel holder by the robotic manipulator, an RFID writer may write the information on the RFID tag that the respective vessel holder is empty. Subsequently, an RFID reader being part of the empty vessel holder detector of the empty vessel holder detection unit may detect this information on the respective vessel holder such that the transfer initiator of the empty vessel holder detection unit may initiate the introduction or re-introduction of the empty vessel holder into the storage module by the empty vessel holder transfer unit.

The identification tag in FIG. 4 may be an RFID tag onto which the empty vessel holder detector (11) may write the information whether the vessel holder is empty or holds a vessel (2) containing a biological sample, based on the weighing result. This information may then be read by a suitable RFID reader being part of the transfer initiator (12), and empty vessel holders (7) may then be directed to the storage module (6).

The automated system can also involve embodiments in which the kinetic properties of vessel holders can be analyzed, as the latter can depend on whether the vessel holders hold a vessel containing a biological sample or whether the vessel holders are empty. One of these kinetic properties, as known by the skilled person, can be velocity. The velocity of a vessel holder holding a vessel containing a biological sample may be decreased when compared to an empty vessel holder because of the additional mass that has to be accelerated by the transport medium, particularly in embodiments where the transport medium is a magnetic surface and the vessel holders are not transported with a constant speed, but depend on acceleration by dynamic electromagnetic fields. Hence, in some embodiments of the automated system described herein, the empty vessel holder detector can comprise a velocity sensor for measuring the relative or absolute velocity of a vessel holder.

The simplest form of measuring the average velocity of an object can be to determine the amount of time it can require to move from one predetermined location to another, and to divide the covered distance by that amount of time. A velocity sensor exploiting this principle thus can comprise detecting the object, such as a vessel holder, at the respective predetermined points, and to measure the time elapsed between detection at the first and detection at the second predetermined point.

Figure 5:
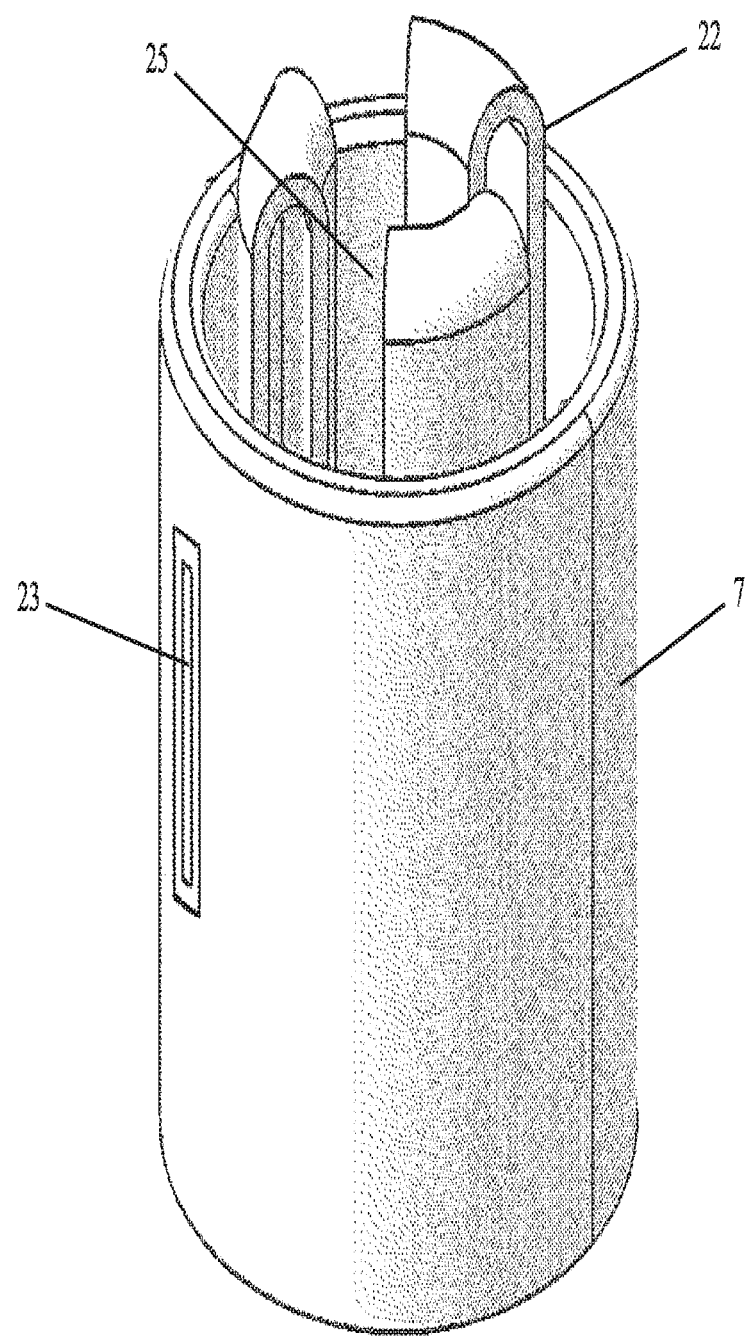
FIG. 5 illustrates a single empty member of the plurality of vessel holders according to an embodiment of the present disclosure.

FIG. 5 depicts a single empty vessel holder (7) equipped with an identification tag (23) in the form of an RFID tag which may carry re-writable information about the vessel holder being empty or holding a vessel (2), such that a transfer initiator (12) having an RFID reader may recognize empty vessel holders (7) and initiate their introduction into the storage module (6). According to the shape of the vessel holder (3) in this embodiment, it may also be referred to as puck. For holding the vessel (2) containing a biological sample by press-fit, the empty vessel holder (7) in this embodiment can have three clamps (22) arranged in a circle around a free space (25) thus forming a socket designated for receiving the vessel (2) containing a biological sample.

Storage Module

The storage modules of the automated system can have different shapes and sizes. It is to be understood that they may be used not only in the context of the automated system and the method described but also in other systems and methods involving vessel holders.

Figure 6A:
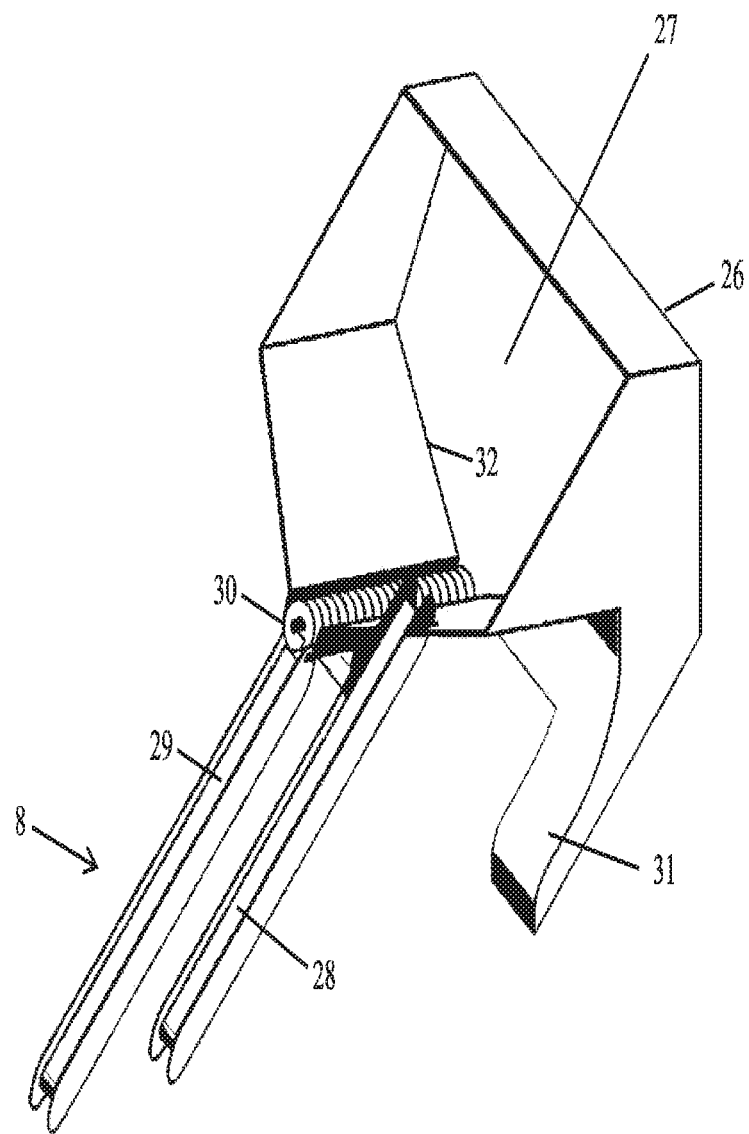
FIGS. 6A-C illustrate the storage module as a bulk container according to an embodiment of the present disclosure.
Figure 6B:
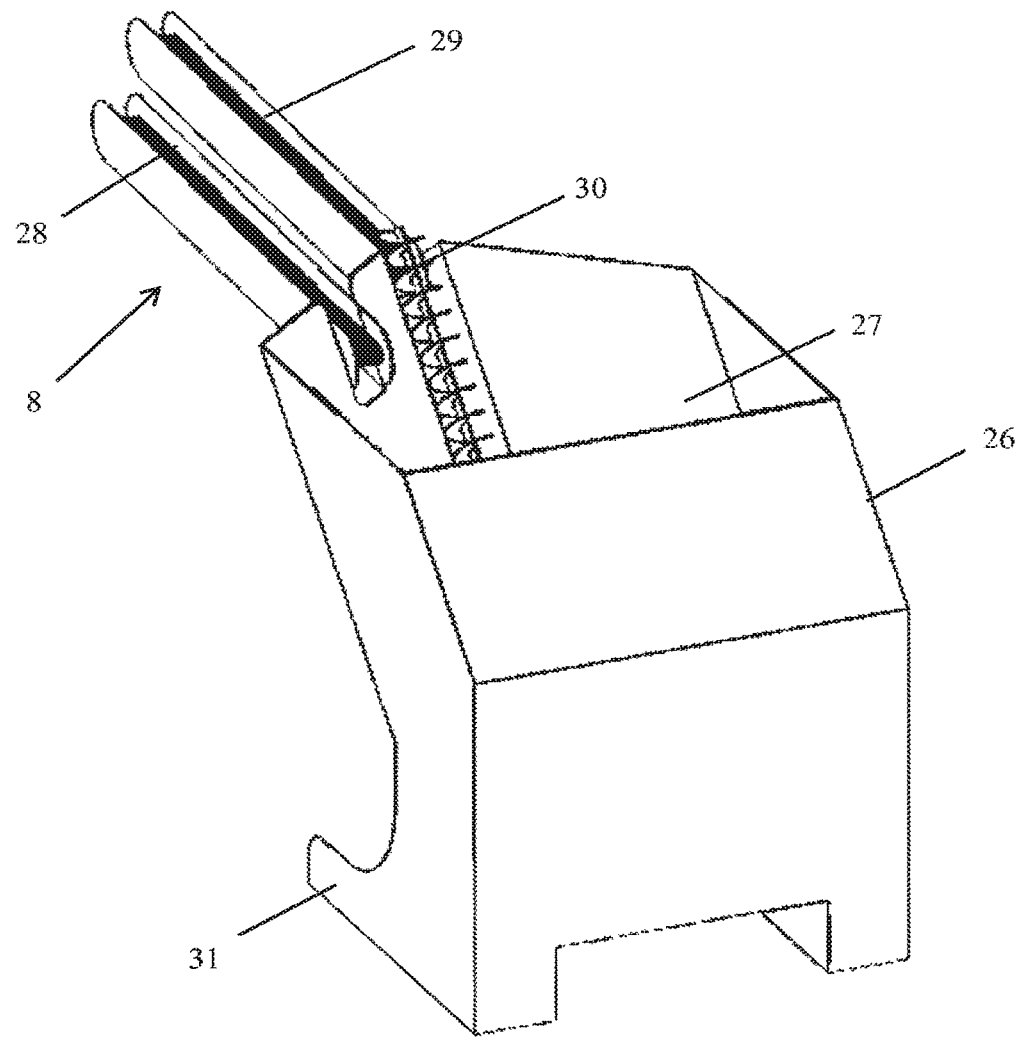
Figure 6C:
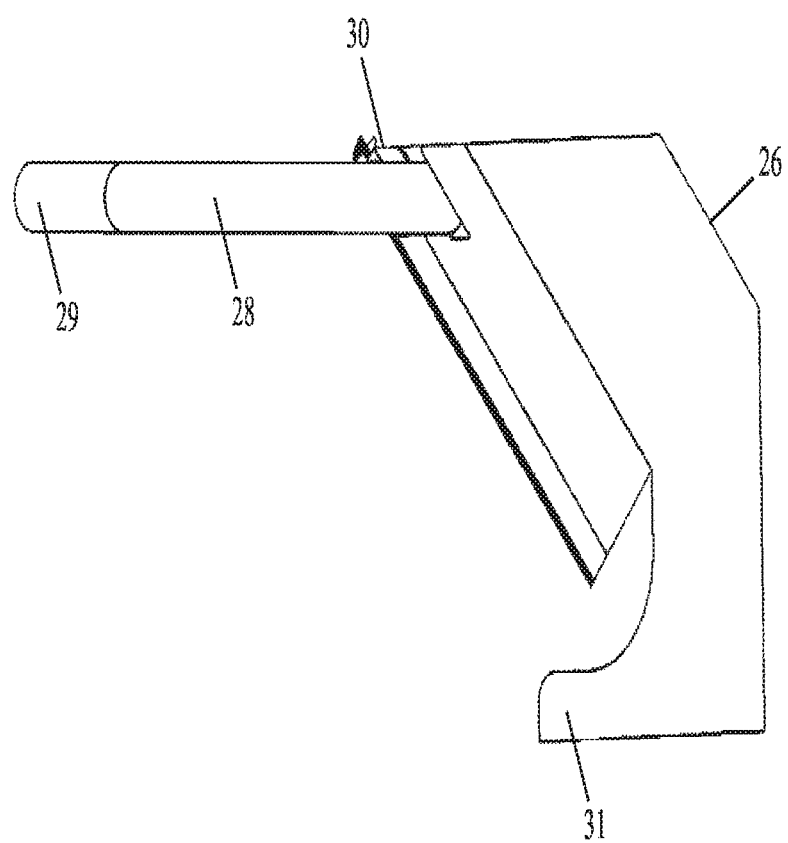

In one of the simplest embodiments, the storage module can be a bulk container in which the empty members of the plurality of vessel holders can be stored in an unstructured manner. FIGS. 6A-C show such an embodiment in which the storage module (6) is a bulk container (26).

FIG. 6A shows a perspective view of the bulk container (26). The essentially unstructured inner space (27) can be designated to receive and store the empty members (7) of the plurality of vessel holders (3). The protrusion (31) can help stabilizing the bulk container (26) when standing on an even surface. In the depicted embodiment, the empty vessel holder transfer unit (8) can have two connecting lines (28, 29) in the form of band conveyors. Their respective moving direction is indicated by the arrows. The first connecting line (28) can be arranged to introduce the empty members (7) of the plurality of vessel holders (3) into the bulk container (26). Its one end can extend slightly over the upper rim of the bulk container (26) such that the empty members (7) of the plurality of vessel holders (3) that are transported along the first connecting line (28) can fall into the bulk container (26). The inner walls of the bulk container (26) can be inclined at an angle, such as to form a depression (32) at the bottom of the inner space (27) in which the empty vessel holders (7) can accumulate and eventually pile up. The second connecting line (29) can transport empty vessel holders (7), when needed, to the transport medium (4). It can be fed via a conveying screw (30) extending from the bottom depression (32) of the inner space (27) of the bulk container (26) to its upper rim, where it can end into the second connecting line (29). In other words, the conveying screw (30) can transport the empty members (7) of the plurality of vessel holders (3) from the inner space (27) of the bulk container (26) to the empty vessel holder transfer unit (8) in order to provide the empty vessels (7) to the transport medium (4) when needed. The conveying screw (30) may include an adjusting mechanism in order to deliver the empty vessel holders (7) in the correct orientation. A correct orientation can mean that it may be possible to place the respective vessel (2) into the empty holder (3). In the case of the empty vessel holders (7) in FIGS. 2-5, this can imply that they contact the surface on which they stand with their bottom, not with their opening (25) that can remain accessible for the respective vessels (2). In some embodiments, the correct orientation may be ensured by mechanical means. For example, the lower end of the spiral conveyor (30) may include a gate which may due to its shape only be passed by empty vessel holders (7) in the correct orientation. A more complex solution may involve a sensor detecting the current orientation of an empty vessel holder (7), and a mechanism such as a robotic gripper adjusting those empty vessel holders (7) that are currently not in the correct orientation.

FIG. 6B shows the bulk container (26) in a perspective view from a different perspective. The windings of the conveying screw (30) ending into the second connecting line (29) are visible in this view.

FIG. 6C shows the bulk container (26) in a lateral view. Due to the shape of the bulk container (26), the second connecting line (29) fed by the conveying screw (30) can extend longer than the first connecting line (28) and can thus be still visible behind the first connecting line (28). It can be seen how the protrusion (31) can contribute to stabilizing the bulk container (26) when standing on an even surface, as it can extend the contact area between surface and container (26) further towards the balance point of the latter.

Alternatively, the storage module can contain the empty members of the plurality of vessel holders in a predefined geometrical arrangement. For instance, the predefined geometrical arrangement may in some embodiments be one-dimensional, i.e. the empty members of the plurality of vessel holders line up in one specific direction. In such an embodiment, a band conveyor may extend through the storage module. If the width of the band is sufficient for only one empty vessel holder at a time, then the empty vessel holders can form a line along the length of the band conveyor, leading to the one-dimensional arrangement. The storage module may also, in other embodiments, contain the empty members of the plurality of vessel holders in a two-dimensional predefined geometrical arrangement. In such a case, the empty vessel holders can be arranged in a plane, for example in a matrix such as an 8×12 or any other suitable matrix, in which the empty vessel holders can form rows along an x-axis and columns along a y-axis. In some embodiments, the storage module may contain the empty members of the plurality of vessel holders in a three-dimensional predefined geometrical arrangement. Hence, the empty vessel holders can be distributed also along a z-axis in addition to the x- and y-axes. For instance, the empty vessel holders may be stacked in multiple planes in the z-axis.

In order to facilitate the workflow with regard to introducing empty vessel holders into the storage module or retrieving them therefrom, the storage module of the automated system can, in some embodiments, be rotatable and/or comprise rotatable parts for positioning the empty members of the plurality of vessel holders with respect to the empty vessel holder transfer unit.

Accordingly, also described is a storage module of an automated system for processing vessels containing biological samples, wherein the storage module can comprise a plurality of empty vessel holders for use in the automated system, and wherein the storage module can be rotatable and/or comprises rotatable parts.

For instance, if the empty vessel holders are arranged on a disk-shaped bottom included by the storage module and a conveyor band of the empty vessel holder transfer unit is positioned at a specific location with regard to said disk-shaped bottom, then it may be advantageous if the latter can be rotatable such that empty vessel holders can be moved towards the position of the conveyor band by rotation of the disk-shaped bottom.

In other embodiments of the automated system, the storage module can comprise a rotatable drum, the rotatable drum comprising multiple tubes aligned at a radius of the rotational axis of the drum, wherein the empty members of the plurality of vessel holders can be stacked vertically within the tubes.

In such embodiments, each tube can have a proximal and a distal end, one or both of which may be open such that the empty vessel holder transfer unit can introduce empty vessel holders into the tube or retrieve them therefrom. The tubes may include one or more actuators for moving the empty vessel holders vertically within the tubes, and/or for moving them from the tube to the empty vessel holder transfer unit or vice versa.

Figure 7A:
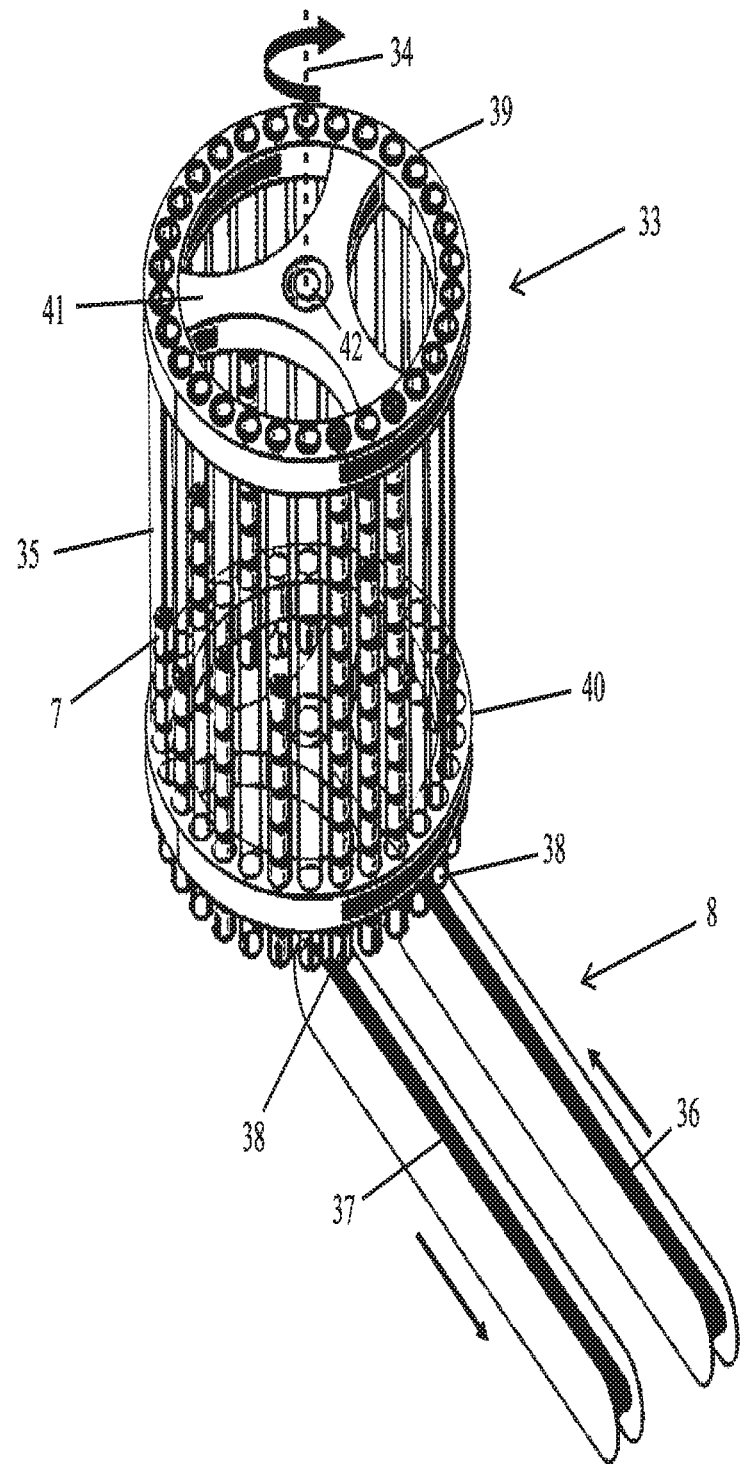
FIGS. 7A-C illustrate the storage module as a multi-tube dispenser in the form of a rotatable drum according to an embodiment of the present disclosure.
Figure 7B:
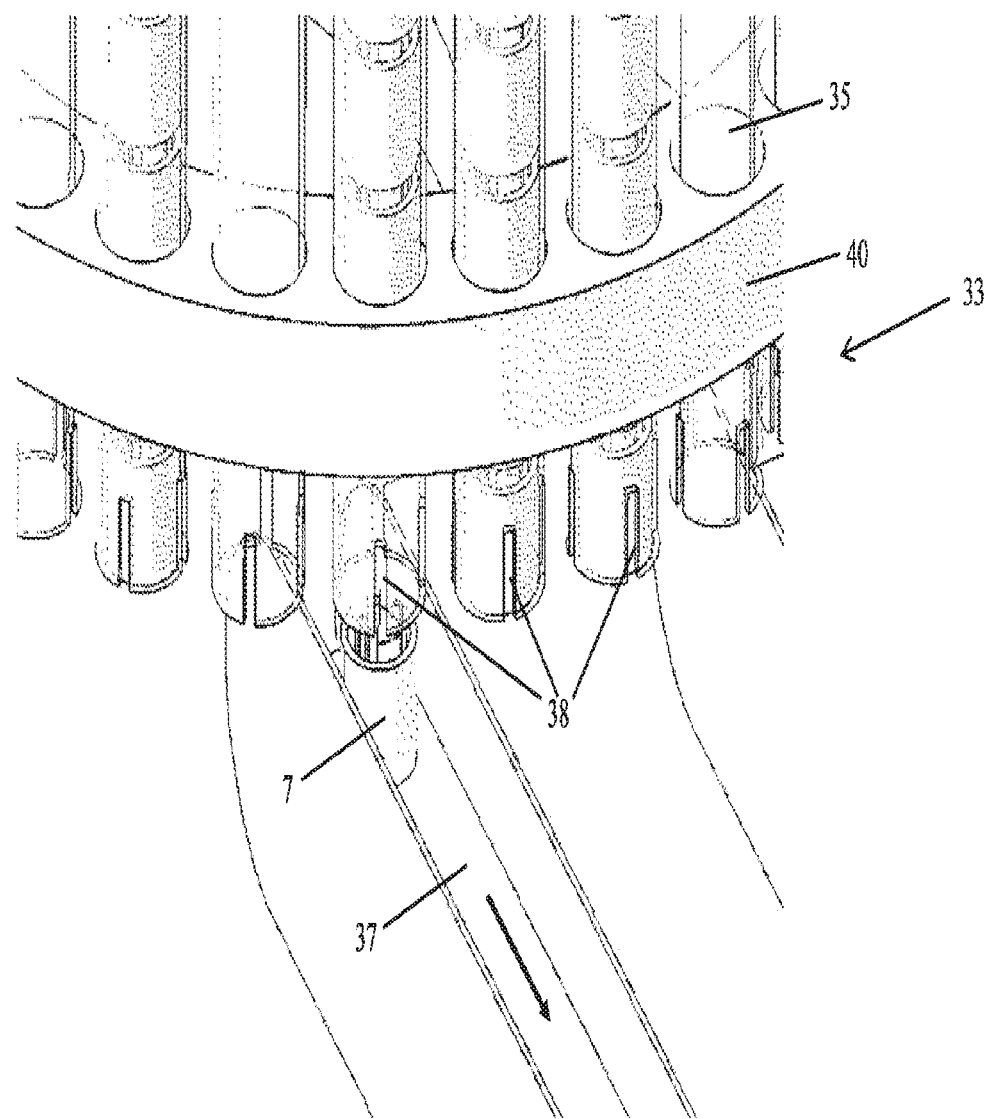
Figure 7C:
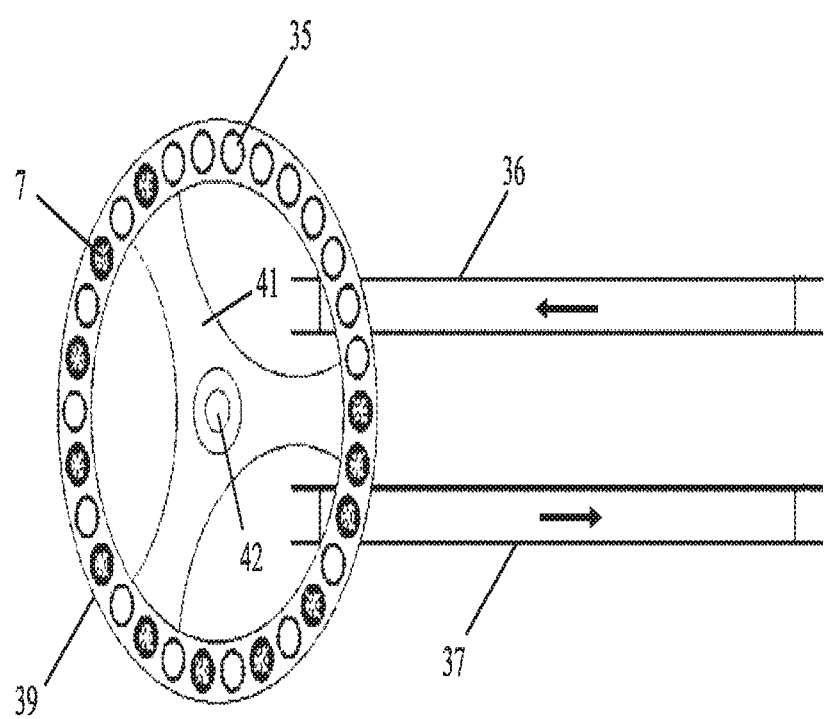

FIGS. 7A-C show an embodiment in which the storage module (6) is a multi-tube dispenser (33) in the form of a rotatable drum. FIG. 7A depicts the dispenser (33) in a perspective view from above. The drum (33) can be rotatable around its rotational axis (34). A direction of rotation is indicated by the circular arrow. The drum (33) can have a plurality of tubes (35) for storing and dispensing empty members (7) of the plurality of vessel holders (3). The tubes (35) can be aligned at a radius of the rotational axis (34) of the drum (33) and can be held by upper (39) and lower (40) rings, each ring having a rim (41) as a central scaffold to thus create a wheel-like structure. The rim (41) can have a gap (42) in its center for interaction with a rotational actuator (not shown) along the drum's (33) rotational axis (34). As can be seen, some of the tubes (35) can be completely or partially filled, while others can be empty. By rotating the drum (33), the appropriate tubes (35) can be positioned above the two conveyor bands serving as connecting lines (36, 37) constituting the empty vessel holder transfer unit (8). For instance, an empty or partially filled tube (35) can be positioned above the first connecting line (36, arrow indicates moving direction of the conveyor band) arranged to introduce empty vessel holders (7) into the drum (33). The lower end of the tube (35) can include a gate (38) that can allow entry or exit of empty vessel holders (7) into or out of the tubes (35). Hence, an empty vessel holder (7) provided to the drum (33) from the transport medium (4) via the empty vessel holder transfer unit's (8) first connecting line (36) can be introduced into the respective tube (35) located above the first connecting line (36) via the gate (38) and stored inside the tube (35) until further use. On the other hand, a filled or partially filled tube (35) may be positioned above the second connecting line (37, arrow indicates moving direction) arranged to retrieve empty vessel holders (7) from the drum (33) to the transport medium (4, not shown), such that an empty member (7) of the plurality of vessel holders (3) can be dropped or actively retrieved from the tube (35) onto the second connecting line (37) for transfer to the transport medium (4). The tubes (35) may include an actuator for moving the empty members (7) of the plurality of vessel holders (3) in vertical direction. Alternatively, the empty vessel holders (7) within the tubes (35) may only be exposed to gravity instead of to an actuator. In alternative embodiments, one or more connecting lines may end into the upper ends of the tubes (35). In other embodiments, the first connecting line (36) may end into the upper ends of the tubes (35) such as to drop empty vessel holders (7) from the transport medium (4) into the tubes (35) by gravity, and the second connecting line (37) may be arranged at the lower end of the tubes (35) as depicted such that the empty vessel holders (7) can be dropped onto the second connecting line (37) by gravity.

FIG. 7B shows a close-up view of the lower part of the drum (33). The interaction between a tube (35) and the second connecting line (37) can be seen, wherein an empty member (7) of the plurality of vessel holders (3) has been dropped by gravity or actively moved onto the conveyor band constituting the second connecting line (37) via the gate (38). For active transfer of the empty vessel holders (7), for example, a robotic gripper may be used. The gates (38) exhibit multiple cut-outs that may enable a gripper to grip an empty vessel holder (7) by moving its gripper arms through the cut-outs. Such a robotic gripper may also be employed for introducing empty vessel holders (7) located below a tube (35) on the first connecting line (36), exploiting the cut-outs in the gates (38) as described above. Alternatively, the gates (38) may include a mechanism for adjusting their diameter. Such a mechanism may be combined with tubes (35) moveable in vertical direction. In such embodiments, a tube (35) located above an empty vessel holder (7) on the first connecting line (36) may be moved down onto the empty vessel holder (7) until contact is established. Subsequently, the diameter of the corresponding gate (38) may be increased such that the tube (35) may be moved further down until the gate (38) surrounds the empty vessel holder (7), thereby shifting the other empty vessel holders (7) in the tube up. By constraining the gate (38) again to its original dimensions, the empty vessel holder (7) may be taken up into the tube (35) and be kept therein. For retrieval of empty vessel holders (7) from a tube (35), the latter may not have to be moved, but the respective gate (38) may be widened such that the respective empty vessel holder (7) may be dropped onto the second connecting line (37) by gravity. In another embodiment, the tube (35) may be also moved down for retrieval, in this case it may move down until contact of the gate (38) and thus the lowermost empty vessel holder (7) can be established. The gate (38) may then be widened, the tube (35) can be moved back up one position and be then constrained again around the second lowermost empty vessel holder (7), thereby releasing the lowermost empty vessel holder (7) onto the second connecting line (37). In the following, the tube (35) may be moved back up to its original position. In other embodiments, the tubes (35) may include a thread along their inner walls. Empty members (7) of the plurality of vessel holders (3) may be held by such threads. Additionally, such threads may be driven by an actuator so as to cause rotational movement of the threads and thus vertical movement of the empty vessel holders (7) within the tubes (35).

FIG. 7C depicts the rotatable drum (33) with the first (36) and second (37) connecting lines as viewed from above. Some of the tubes (35) can contain empty vessel holders (7). The wheel-like structure composed of the upper ring (39) and its central rim (41) including the gap (42) can be seen from the top.

Also, in some embodiments of the automated system, the storage module can comprise a rotatable spiral conveyor along which the empty members of the plurality of vessel holders can be aligned. For advantageous usage of the available space within the storage module and thus within the automated system described, in some embodiments multiple spiral conveyors can be stacked vertically to form multiple layers. The conveyors can be, in some embodiments, connected to each other, such that the empty vessel holders can be transported across the different layers. Also in some embodiments, one or more spiral conveyors can extend in vertical direction like a helix, such that empty vessel holders can be transported vertically along the spiral or spirals.

Figure 8B:
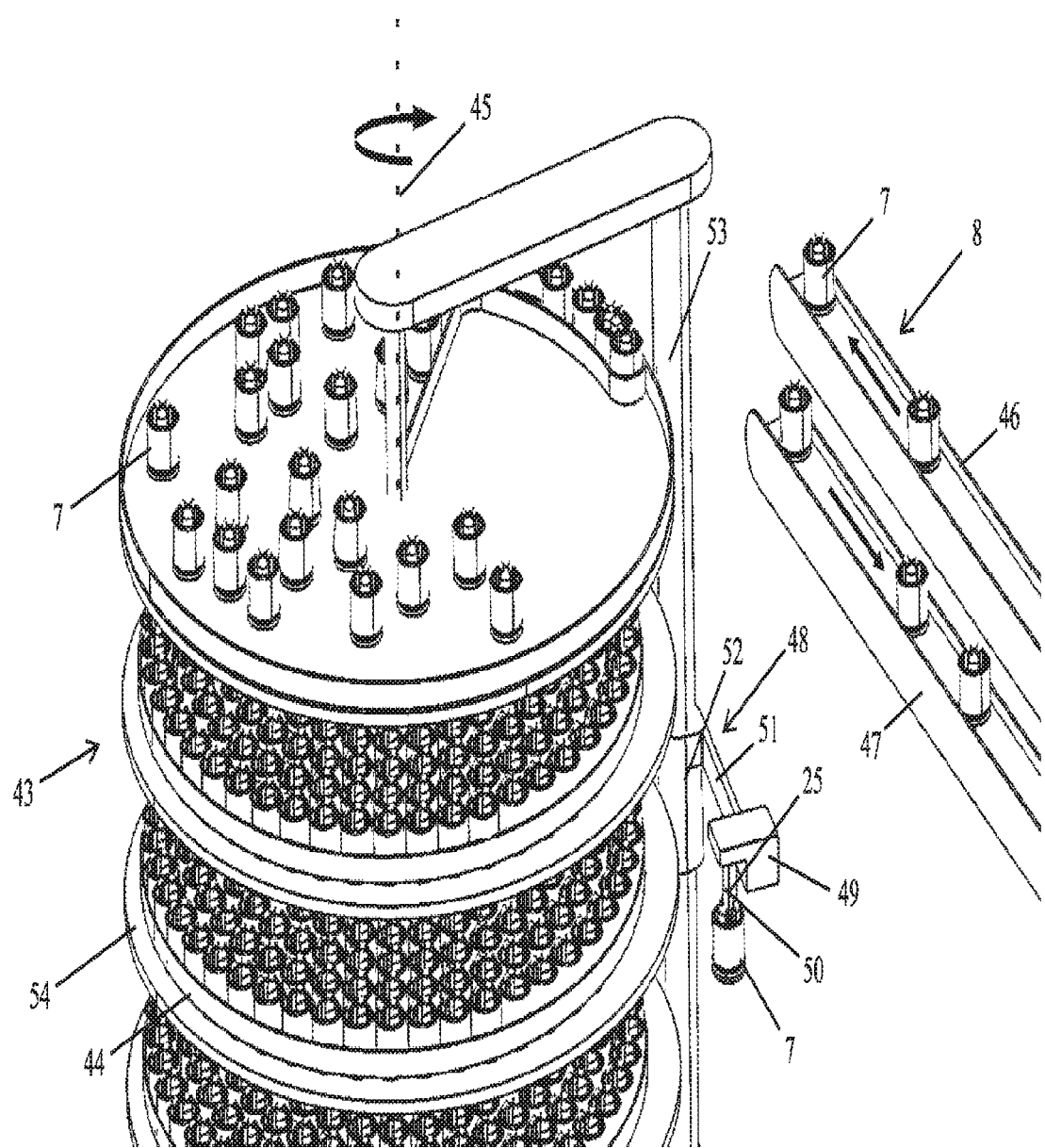
Figure 8C:
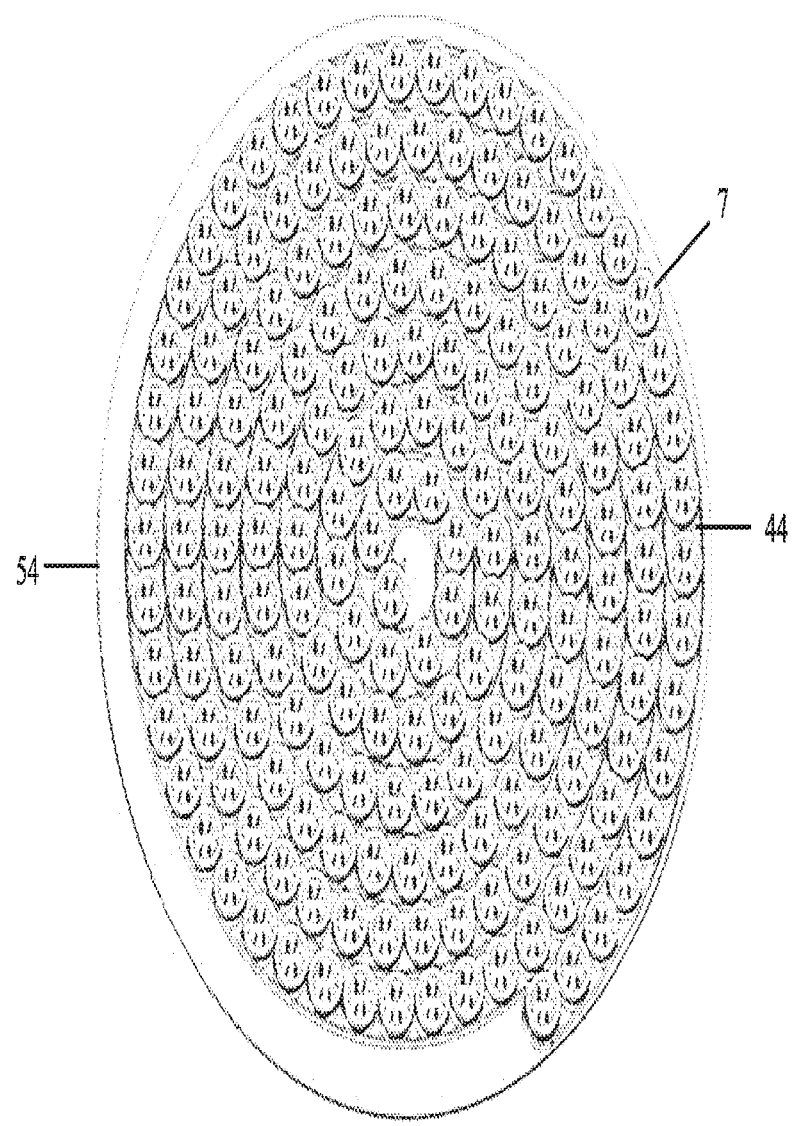

FIG. 8A-C depicts an embodiment in which the storage module (6) is a cylinder-shaped silo (43). As can be seen in FIG. 8A, the silo (43) can include multiple spiral conveyors (44) stacked in vertical direction. The single conveyors (44) may be rotatable individually, and/or the silo (43) as a whole may be rotatable around the rotational axis (45). In the multiple layers formed by the spiral conveyors (44), empty members (7) of the plurality of vessel holders (3) can be stored along the spiral conveyors (44). When needed, empty vessel holders (7) can be retrieved from one of the spiral conveyors (44) and placed on the empty vessel holder transfer unit (8). The latter in this embodiment can have two conveyor bands, one of which forming a first connecting line (46) for introducing the empty members (7) of the plurality of vessel holders (3) detected in or on the transport medium (4) into the silo (43), the other one forming a second connecting line (47) for retrieving empty vessel holders (7) from the silo (43) in order to place them on the transport medium (4) when needed. Their respective moving directions are indicated by arrows. The empty vessel holder transfer unit (8) in this embodiment can further include a vertically and laterally moveable shuttle system (48), in which a handler (49) having a bolt (50) can be fixed to a collar (52) via an arm (51). The collar (52) can embrace a vertical guide bar (53) along which it can be arranged to glide in vertical direction, such that the handler (49) can be able to reach the empty vessel holders (7) in all of the disc-shaped compartments (54) holding the multiple spiral conveyors (44). The collar (52) can further permit the shuttle system (48) to move in lateral direction by rotating around the axis constituted by the vertical guide bar (53). It can be seen in the current depiction that the bolt (50) of the handler (49) can be located above an empty member (7) of the plurality of vessel holders (3). More precisely, the bolt (50) has been brought in an appropriate position to be introduced into the vessel socket (25) formed by clamps (22). The empty vessel holder (7) can then be picked up by the handler (49) by press-fitting the bolt (50) into the socket (25), such that the empty vessel holder (7) can now be introduced into the silo (43) via the empty vessel holder shuttle system (48) of the empty vessel holder transfer unit (8). For releasing the empty vessel holder (7) from the bolt (50) of the handler (49), the latter may include a mechanism to push the empty vessel holder (7) away from the bolt (50). Such a mechanism may involve extendable pens arranged around the bolt (50) in a manner that they can exert pressure on the clamps (22) of the empty vessel holder (7). In the depicted embodiment, the handler (49) may be arranged to slide along the arm (51) to provide further lateral mobility. In this case, the holder (49) may place empty members (7) of the plurality of vessel holders (3) retrieved from the silo (43) on the second connecting line (47) by sliding the holder (49) with the bolt (50) into the appropriate position. However, in this embodiment, this positioning may also be achieved by rotating the arm (51) to place the holder (49) with the bolt (50) above the second connecting line (47). In some embodiments, the arm (51) may be a telescope arm, such that also more distant portions of the multiple spiral conveyors (44) may be reached by the handler (49). In some embodiments, one of the connecting lines may be arranged in a different vertical position, such as one at the bottom and the other one at the top of the silo (43), and there may be more than one shuttle. It is also possible that only one connecting line can be used for both introducing and retrieving empty vessel holders (7). In further embodiments, the silo (43) may have one big spiral conveyor extending vertically over several levels in a helix-like structure, as opposed to stacks of multiple spiral conveyors (44).

FIG. 8B shows the handler (49) holding an empty vessel holder (7) with its bolt (50) introduced into the vessel socket (25). The handler (49) has been moved vertically to a lower position as compared to the position in FIG. 8A, by sliding the collar (52) along the vertical guide bar (53). Also, the handler (49) has been rotated clockwise about 90° in relation to the former figure around the rotational axis constituted by the vertical guide bar (53). In the depicted position, the holder (49) may either deliver the empty vessel holder (7) to a free storage space in a spiral conveyor (44) of the silo (43), or it may place it on the second connecting line (47) of the empty vessel holder transfer unit (8) for transferring the empty vessel holder (7) to the transport medium (4). For dropping the empty vessel holder (7), the bolt (50) can be retrieved from the vessel socket (25) by an appropriate mechanism comprised by the holder (49).

FIG. 8C shows a top view of one spiral conveyor (44) of the silo (43) containing empty members (7) of the plurality of vessel holders (3). The spiral arrangement bringing about efficient usage of the storage space while assuring good accessibility for the handler (49) is visible. The spiral conveyor (44) may be driven by an actuator. In some embodiments, the spiral conveyor (44) can be a spiral band-conveyor. For instance, empty vessel holders (7) retrieved from the outermost row of the spiral may be replaced by the conveyor moving towards the outer end of the spiral, such that there can be a constant supply of empty vessel holders (7) in the outermost row of the spiral until no empty vessel holders (7) are left on the respective spiral conveyor (44). In the case of only partially filled spiral conveyors (44), empty vessel holders (7) can be introduced into the silo (43) via the shuttle system (48) by placing it on the outer portion of the spiral may be transported to the inner part of the spiral conveyor (44) such that the space on the outer portion becomes available again for further empty vessel holders (7) to be introduced into the silo (43). In another embodiment, the spiral conveyor (44) may or may not be a band-conveyor as described above, while the disc-shaped compartment (54) can be rotated around rotational axis 45 shown in FIG. 8A and FIG. 8B. In cases where the handler (49) does not extend further than axis 45, rotation of the compartment (54) may facilitate the availability of empty vessel holders (7) on the side of the compartment (54) facing the guide bar (53) even during constant retrieval of empty vessel holders (7), as long as empty vessel holders (7) are present in the compartment (54).

Method for Processing Vessels

A method for processing vessels containing biological samples in an automated system is presented. The method can comprise retrieving an empty vessel holder to a transport medium from a storage module comprising a plurality of empty vessel holders. The storage module can be connected to the transport medium via an empty vessel holder transfer unit for introducing empty vessel holders from the transport medium into the storage module or retrieving them from the storage module to the transport medium. A biological sample can be engaged to the retrieved empty vessel holder. The vessel holder with the engaged vessel containing a biological sample can be transported via the transport medium to a work cell. The vessel containing a biological sample can be processed within the work cell. The vessel containing a biological sample can be disengaged from the vessel holder. The empty vessel holder can be detected by an empty vessel holder detection unit for detecting empty vessel holders in or on the transport medium. The empty vessel holder detection unit can comprise an empty vessel holder detector for discriminating between filled and empty vessel holders. A transfer initiator can be configured to initiate the introduction or re-introduction of an empty vessel holder detected in or on the transport medium into the storage module by the empty vessel holder transfer unit. The empty vessel holder can be re-introduced into the storage module.

As set out above in the context of the automated system described herein, the active detection and subsequent removal of vessel holders from which the vessel containing a biological sample has been removed and placing them into a dedicated storage module, can facilitate an efficient workflow and can prevent spatial and computer-related capacities from being taken up by the identification and transportation of empty vessel holders in or on the transport medium.

In some embodiments of the method, any empty vessel holder in or on the transport medium can be detected by the empty vessel holder detection unit and can subsequently be introduced or re-introduced into the storage module.

In this embodiment, vessel holders that are empty for other reasons than interaction with the robotic manipulator for engaging/disengaging the vessels containing biological samples can be likewise detected by the empty vessel holder detector of the empty vessel holder detection unit, thus the transfer unit of by the empty vessel holder detection unit can subsequently initiate the introduction of the empty vessel holders into the storage unit via the empty vessel holder transfer unit.

In some embodiments of the method, each vessel holder can comprise an identification tag for detection by the empty vessel holder detection unit.

The embodiments disclosed in the context of the automated system can also be applicable to the method described herein.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An automated system for processing vessels containing biological samples, the automated system comprising:
   a plurality of vessel holders for the vessels containing biological samples;
   a transport medium for transporting the vessel holders within the automated system;
   a work cell for processing the vessels containing biological samples;
   a storage module for empty members of the plurality of vessel holders, wherein the storage module is connected to the transport medium via an empty vessel holder transfer unit, which comprises a vertical and lateral moving shuttle system, and is configured for retrieving empty vessel holders from the transport medium and introducing them into the storage module, or retrieving empty vessel holders from the storage module and placing them in or on the transport medium;
   a robotic manipulator for engaging and/or disengaging the vessels containing biological samples with the empty members of the plurality of vessel holders;
   a control unit for controlling the automated system; and
   an empty vessel holder detection unit configured for detecting empty vessel holders in or on the transport medium, the empty vessel holder detection unit comprising an empty vessel holder detector for discriminating between filled and empty vessel holders, and a transfer initiator configured to initiate the introduction or re-introduction of an empty vessel holder detected in or on the transport medium into the storage module by the empty vessel holder transfer unit.

2. The automated system of claim 1, wherein the storage module is a bulk container.

3. The automated system of claim 1, wherein the empty vessel holder detector comprises a mechanical, electrical, electromechanical, electromagnetic, or optical detection system.

4. The automated system of claim 3, wherein the optical detection system comprises a camera.

5. The automated system of claim 1, wherein the empty vessel holder detector comprises a weighing system.

6. The automated system of claim 5, wherein the weighing system comprises a balance integrated in the transport medium.

7. The automated system of claim 1, wherein the empty vessel holder detector comprises a mechanical barrier located in a position relative to a vessel holder circulating in or on the transport medium, wherein the first position intersects a vessel's track that it travels along the transport medium if present in the vessel holder such that a vessel in the vessel holder is deviated by the mechanical barrier relative to an empty vessel holder circulating in or on the transport medium.

8. The automated system of claim 7, wherein the mechanical barrier is positioned no higher than vessel holder itself and no lower than the vessel's track.

9. The automated system of claim 1, wherein each vessel holder comprises an identification tag for detection by the empty vessel holder detection unit.

10. The automated system of claim 9, wherein the identification tag is a barcode or an RFID tag.

11. The automated system of claim 1, wherein the storage module comprises a rotatable drum, the rotatable drum comprising multiple tubes aligned at a radius of the rotational axis of the drum, wherein the empty members of the plurality of vessel holders are stacked vertically within the tubes.

12. A method for processing vessels containing biological samples in an automated system, the method comprising:
   retrieving an empty vessel holder to a transport medium from a storage module comprising a plurality of empty vessel holders, wherein the storage module is connected to the transport medium via an empty vessel holder transfer unit comprising a vertical and lateral moving shuttle system for introducing empty vessel holders from the transport medium into the storage module or retrieving them from the storage module to the transport medium by moving vertically and laterally along the cylinder-shaped silo storage module;
   engaging a vessel comprising a biological sample to the retrieved empty vessel holder;
   transporting the vessel holder with the engaged vessel comprising a biological sample via the transport medium to a work cell;
   processing the vessel containing a biological sample within the work cell;
   disengaging the vessel comprising a biological sample from the vessel holder;
   detecting the empty vessel holder by an empty vessel holder detection unit for detecting empty vessel holders in or on the transport medium, the empty vessel holder detection unit comprising an empty vessel holder detector for discriminating between filled and empty vessel holders, and a transfer initiator configured to initiate the introduction or re-introduction of an empty vessel holder detected in or on the transport medium into the storage module by the vertical and lateral moving shuttle system of the empty vessel holder transfer unit; and
   re-introducing the empty vessel holder into the storage module by moving the empty vessel holder vertically and laterally into the storage module.

13. The method for processing vessels containing biological samples in an automated system according to claim 12, further comprises,
   analyzing kinetic properties of the vessel holders.

14. The method for processing vessels containing biological samples in an automated system according to claim 13, wherein a kinetic property is velocity.

15. The method for processing vessels containing biological samples in an automated system according to claim 12, further comprising,
    detecting each vessel holder by the empty vessel holder detection unit by an identification tag on the each vessel holder.

16. The method for processing vessels containing biological samples in an automated system according to claim 12, further comprising,
    directing empty vessel holders in or on transport medium on a shortest possible route to the storage module by the transfer initiator.

17. The method for processing vessels containing biological samples in an automated system according to claim 12, further comprising,
    arranging the empty vessel holders in a predefined geometrical arrangement within the storage module.

* * * * *